(12) United States Patent
Ferrante et al.

(10) Patent No.: US 7,527,627 B2
(45) Date of Patent: *May 5, 2009

(54) ORTHOPAEDIC IMPLANT AND SCREW ASSEMBLY

(75) Inventors: Joseph Ferrante, Bartlett, TN (US);
Angie Mines, Mason, TN (US);
Anthony H. James, Bartlett, TN (US);
Thomas A. Russell, Collierville, TN (US); Roy Sanders, Tampa, FL (US)

(73) Assignee: Smith & Nephew, Inc., Memphis, TN (US)

( * ) Notice: Subject to any disclaimer, the term of this patent is extended or adjusted under 35 U.S.C. 154(b) by 413 days.

This patent is subject to a terminal disclaimer.

(21) Appl. No.: 10/936,996

(22) Filed: Sep. 8, 2004

(65) Prior Publication Data

US 2005/0149024 A1 Jul. 7, 2005

Related U.S. Application Data

(63) Continuation of application No. 10/658,351, filed on Sep. 8, 2003, now abandoned.

(51) Int. Cl.
*A61B 17/56* (2006.01)
*A61B 17/58* (2006.01)
(52) U.S. Cl. .............................. 606/64; 606/62; 606/68
(58) Field of Classification Search .................... 606/62, 606/63, 64, 65, 66, 67, 68
See application file for complete search history.

(56) References Cited

U.S. PATENT DOCUMENTS

| 2,267,925 A | 12/1941 | Johnston |
| 2,699,774 A | 1/1955 | Harrison |

(Continued)

FOREIGN PATENT DOCUMENTS

BE 551 875 11/1956

(Continued)

OTHER PUBLICATIONS

Brochure entitled "OR manual Platon (tantum))) the medical people," 22 pages, Aug. 2002.

(Continued)

*Primary Examiner*—Pedro Philogene
(74) *Attorney, Agent, or Firm*—Fish & Richardson P.C.

(57) ABSTRACT

Systems, devices and methods are disclosed for treating fractures. The systems, devices and methods may include one or both of an implant, such as an intramedullary nail, and a fastening assembly, such as a lag screw and compression screw assembly. The implant in some embodiments has a proximal section with a transverse aperture and a cross-section that may be shaped to more accurately conform to the anatomical shape of cortical bone and to provide additional strength and robustness in its lateral portions, preferably without requiring significant additional material. The fastening assembly may be received to slide, in a controlled way, in the transverse aperture of the implant. In some embodiments, the engaging member and the compression device are configured so that the compression device interacts with a portion of the implant and a portion of the engaging member to enable controlled movement between the first and second bone fragments. This configuration is useful for, among other things, compressing a fracture.

20 Claims, 21 Drawing Sheets

U.S. PATENT DOCUMENTS

| | | | |
|---|---|---|---|
| 3,530,854 A * | 9/1970 | Kearney | 606/67 |
| 4,103,683 A | 8/1978 | Neufeld | |
| 4,172,452 A | 10/1979 | Forte | |
| 4,438,762 A | 3/1984 | Kyle | |
| 4,622,959 A | 11/1986 | Marcus | |
| 4,641,640 A | 2/1987 | Griggs | |
| 4,657,001 A * | 4/1987 | Fixel | 606/66 |
| 4,776,330 A | 10/1988 | Chapman et al. | |
| 4,827,917 A | 5/1989 | Brumfield | |
| 4,978,349 A | 12/1990 | Frigg | |
| 5,032,125 A | 7/1991 | Durham et al. | |
| 5,041,116 A | 8/1991 | Wilson | |
| 5,100,404 A | 3/1992 | Hayes | |
| 5,112,333 A | 5/1992 | Fixel | |
| 5,122,141 A | 6/1992 | Simpson et al. | |
| 5,167,663 A | 12/1992 | Brumfield | |
| 5,176,681 A | 1/1993 | Lawes et al. | |
| 5,312,406 A | 5/1994 | Brumfield | |
| 5,324,292 A | 6/1994 | Meyers | |
| 5,429,640 A | 7/1995 | Shuler et al. | |
| 5,454,813 A | 10/1995 | Lawes | |
| 5,514,137 A | 5/1996 | Coutts | |
| 5,514,138 A | 5/1996 | McCarthy | |
| 5,531,748 A | 7/1996 | De la Caffiniere | |
| 5,562,666 A | 10/1996 | Brumfield | |
| 5,562,667 A | 10/1996 | Shuler et al. | |
| 5,573,536 A | 11/1996 | Grosse et al. | |
| 5,591,168 A | 1/1997 | Judet et al. | |
| 5,653,709 A | 8/1997 | Frigg | |
| 5,658,288 A | 8/1997 | Kim | |
| 5,713,902 A | 2/1998 | Friedl | |
| 5,741,256 A | 4/1998 | Bresina | |
| 5,743,908 A | 4/1998 | Kim | |
| 5,749,872 A | 5/1998 | Kyle et al. | |
| 5,779,704 A | 7/1998 | Kim | |
| 5,810,821 A | 9/1998 | Vandewalle | |
| 5,908,422 A | 6/1999 | Bresina | |
| 5,928,235 A | 7/1999 | Friedl | |
| 6,077,264 A | 6/2000 | Chemello | |
| 6,106,528 A | 8/2000 | Durham et al. | |
| 6,123,708 A | 9/2000 | Kilpela et al. | |
| 6,126,661 A | 10/2000 | Faccioli et al. | |
| 6,139,552 A | 10/2000 | Horluchi | |
| 6,183,474 B1 | 2/2001 | Bramlet et al. | |
| 6,187,007 B1 | 2/2001 | Frigg et al. | |
| 6,221,074 B1 | 4/2001 | Cole et al. | |
| 6,228,086 B1 | 5/2001 | Wahl et al. | |
| 6,235,031 B1 * | 5/2001 | Hodgeman et al. | 606/64 |
| 6,322,591 B1 | 11/2001 | Ahrens | |
| 6,406,477 B1 | 6/2002 | Fujiwara | |
| 6,423,066 B1 * | 7/2002 | Harder et al. | 606/65 |
| 6,443,954 B1 | 9/2002 | Bramlet et al. | |
| 6,461,360 B1 | 10/2002 | Adam | |
| 6,468,278 B1 | 10/2002 | Muckter | |
| 6,511,481 B2 | 1/2003 | von Hoffmann et al. | |
| 6,524,314 B1 | 2/2003 | Dean et al. | |
| 6,533,789 B1 | 3/2003 | Hall, IV et al. | |
| 6,562,042 B2 | 5/2003 | Nelson | |
| 6,645,209 B2 | 11/2003 | Hall, IV et al. | |
| 6,648,889 B2 | 11/2003 | Bramlet et al. | |
| 6,652,529 B2 * | 11/2003 | Swanson | 606/62 |
| 6,719,759 B2 | 4/2004 | Wagner et al. | |
| 6,755,832 B2 | 6/2004 | Happonen et al. | |
| 6,902,567 B2 | 7/2005 | Del Medico | |
| 6,932,818 B2 | 8/2005 | Behrens | |
| 7,135,023 B2 * | 11/2006 | Watkins et al. | 606/65 |
| 2002/0032445 A1 | 3/2002 | Fujiwara | |
| 2002/0107578 A1 | 8/2002 | Speitling et al. | |
| 2002/0111629 A1 | 8/2002 | Phillips | |
| 2002/0133156 A1 | 9/2002 | Cole | |
| 2002/0143334 A1 | 10/2002 | Hoffmann et al. | |
| 2002/0156473 A1 | 10/2002 | Bramlet et al. | |
| 2003/0004514 A1 | 1/2003 | Frigg et al. | |
| 2003/0069582 A1 | 4/2003 | Culber | |
| 2003/0074000 A1 | 4/2003 | Roth et al. | |
| 2003/0195515 A1 | 10/2003 | Sohngen | |
| 2004/0010255 A1 | 1/2004 | Warburton | |
| 2004/0127898 A1 | 7/2004 | Adam | |
| 2005/0010223 A1 | 1/2005 | Gotfried | |
| 2005/0055024 A1 | 3/2005 | James et al. | |
| 2005/0070902 A1 | 3/2005 | Medoff | |
| 2005/0101959 A1 | 5/2005 | Mitkovic | |
| 2005/0131411 A1 | 6/2005 | Culbert | |
| 2005/0149024 A1 | 7/2005 | Ferrante et al. | |
| 2005/0149025 A1 | 7/2005 | Ferrante et al. | |
| 2005/0177158 A1 | 8/2005 | Doubler et al. | |
| 2005/0234457 A1 | 10/2005 | James et al. | |
| 2006/0036248 A1 | 2/2006 | Ferrante et al. | |
| 2006/0084999 A1 | 4/2006 | Aschmann | |
| 2007/0270845 A1 | 11/2007 | Watanabe | |
| 2007/0299447 A1 | 12/2007 | Watanabe | |
| 2008/0004623 A1 | 1/2008 | Ferrante | |
| 2008/0033430 A1 | 2/2008 | James | |

FOREIGN PATENT DOCUMENTS

| | | |
|---|---|---|
| DE | 197 23 339 C2 | 12/1998 |
| DE | 198 29 228 C | 10/1999 |
| EP | 0 355 411 A1 | 2/1990 |
| EP | 0441 577 A2 | 8/1991 |
| EP | 0 551 846 A1 | 7/1993 |
| EP | 586 824 | 3/1994 |
| EP | 0 640 318 A1 | 3/1995 |
| EP | 0 486 483 B1 | 2/1996 |
| EP | 0 853 923 B1 | 7/1996 |
| EP | 0 838 199 A1 | 4/1998 |
| EP | 00715832 B1 | 1/2002 |
| EP | 01175872 A2 | 1/2002 |
| EP | 1 273 271 A2 | 6/2002 |
| FR | 2 873 913 | 2/2006 |
| JP | 09 066061 | 3/1997 |
| JP | 2002 065687 | 3/2002 |
| JP | 2003 038508 | 2/2003 |
| WO | WO 95/26688 | 10/1995 |
| WO | WO 97/08999 | 3/1997 |
| WO | WO 97/18769 | 5/1997 |
| WO | WO 01/39679 A1 | 12/1999 |
| WO | WO 00/76414 A1 | 12/2000 |
| WO | WO 01/56487 | 8/2001 |
| WO | WO 01/56487 A1 | 8/2001 |
| WO | WO 01/91660 | 12/2001 |
| WO | WO 01/34045 A1 | 5/2002 |
| WO | WO 02/078555 A1 | 10/2002 |
| WO | WO 02/085219 | 10/2002 |
| WO | WO 02/085228 A1 | 10/2002 |
| WO | WO 03/015649 A1 | 2/2003 |
| WO | WO 03/022166 A1 | 3/2003 |
| WO | WO 03/028567 | 4/2003 |
| WO | WO 03/032852 | 4/2003 |
| WO | WO 2004/110292 | 12/2004 |
| WO | WO 2005/025436 | 3/2005 |
| WO | WO 2005/025437 | 3/2005 |
| WO | WO 2005/034794 A2 | 4/2005 |
| WO | WO 2006/007553 A2 | 1/2006 |
| WO | WO 2007/038560 A1 | 4/2007 |
| WO | WO 2007/109302 | 9/2007 |
| WO | WO 2008/022136 | 2/2008 |

OTHER PUBLICATIONS

Web page entitled, The Platon-Locking-Nail system, numerous improvements, >> one page, Dec. 6, 2003.
Web page entitled The Platon-Locking-Nail system: Quality without compromise, two pages, Jun. 30, 2003.

Ballabarba, et al., Percutaneous Treatment of Peritrochanteric Fractures Using the Gamma Nail, *Clin. Ortho.*, 375:30-42 (Jun 2000).

Baixauli, et al., "A Reinforced Rigid Fixation Device for Unstable Intertrochanteric Fractures," *Clin. Ortho*, 1(361):205-215 (Apr. 1999).

Elder, et al., "Biomechanical Evaluation of Calcium Phosphate Cement-Augmented Fixation of Unstable Intertrochanteric Fractures," *JOT*, 14(6):386-393 (Aug. 2000).

Roberts, et al., Second Generation Intramedullary Nailing of Subtrochanteric Femur Fractures: A Biomechanical Study of Fracture Site Motion, *JOT.* 16(4) :231-238 (Apr. 2002).

Robinson, et al., Implant-Related Fractures of the Femur Following Hip Fracture Surgery, *JBJS*, 84(7):1116 (2002).

International Search Report in related International Application No. PCT/US2007/006986.

Office Action mailed Jul. 3, 2008 in related U.S. Appl. No. 10/937,075.

International Preliminary Report on Patentability, Application Serial No. PCT/US2007/006986, dated Oct. 2, 2008, 8 pages.

* cited by examiner

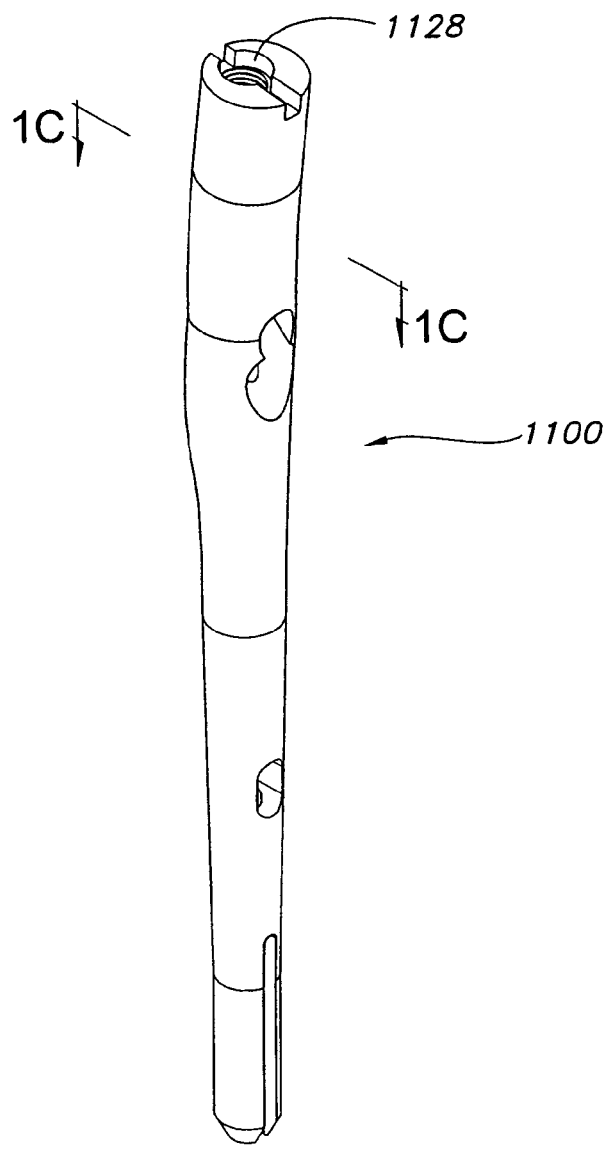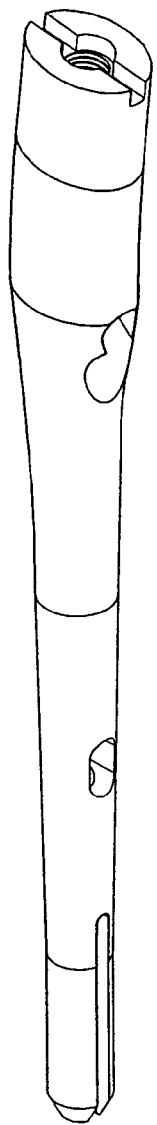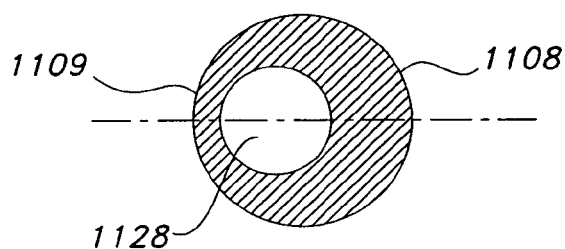
FIG. 1B
FIG. 1D
FIG. 1C

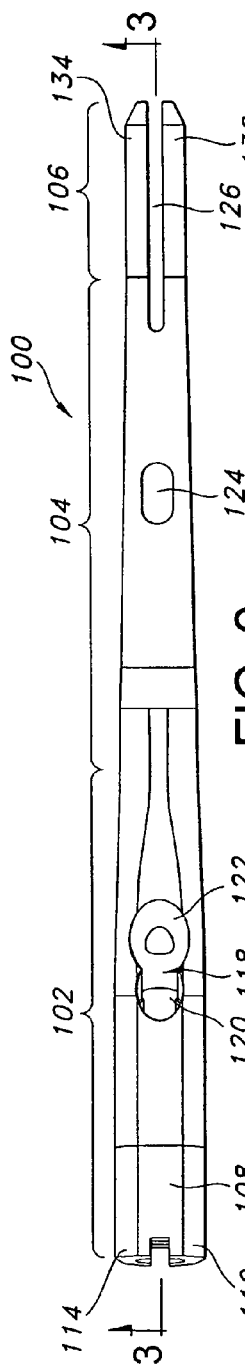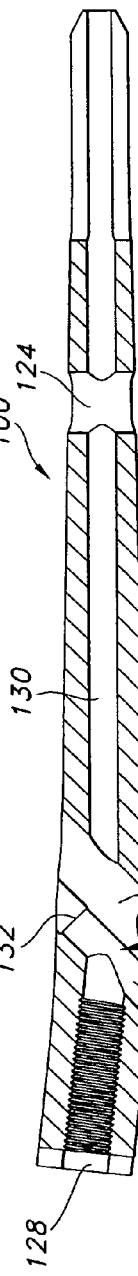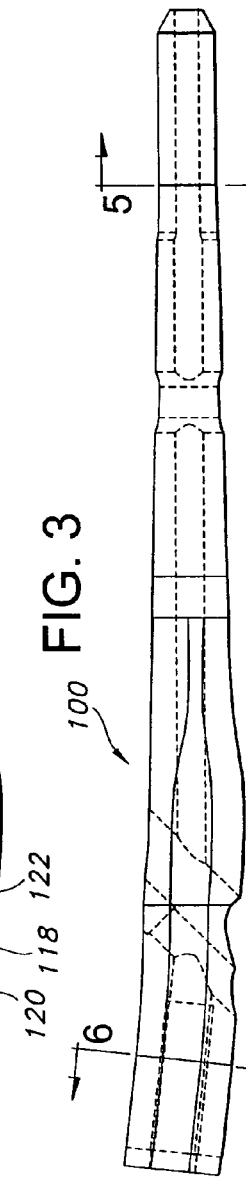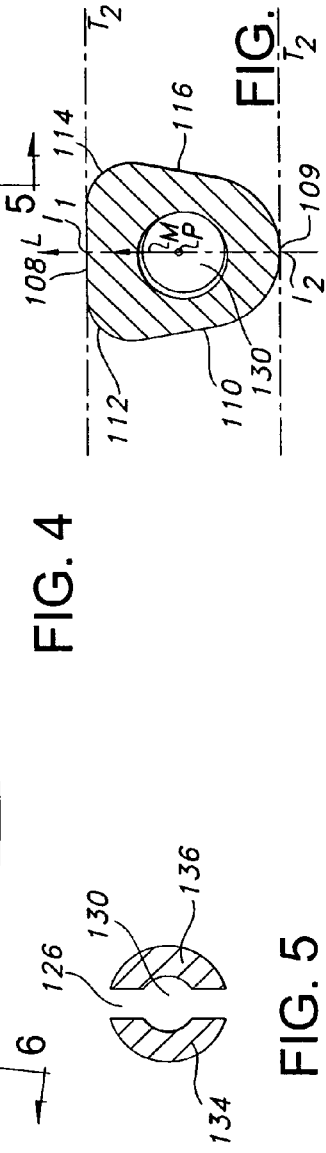
FIG. 2
FIG. 3
FIG. 4
FIG. 5
FIG. 6

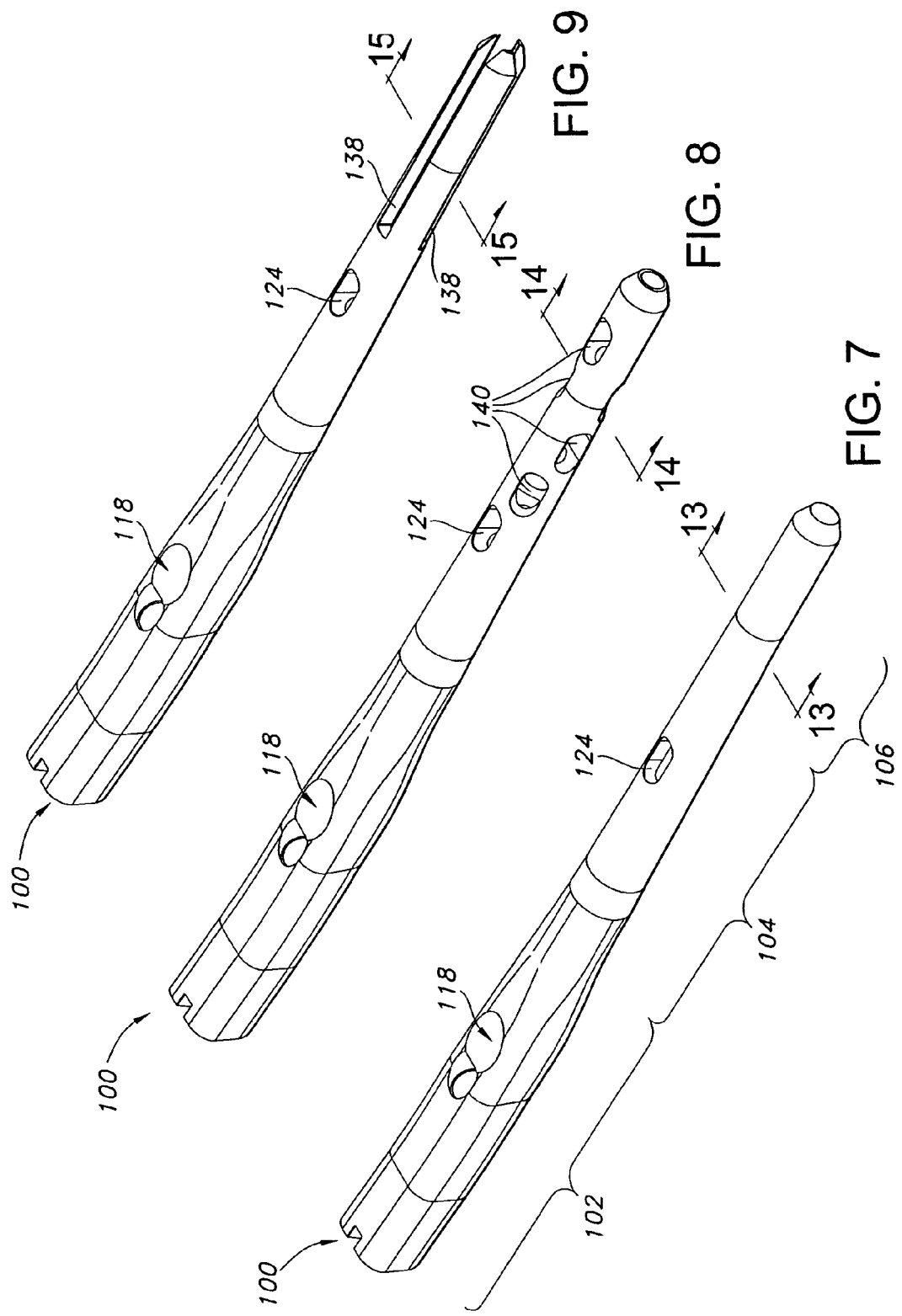

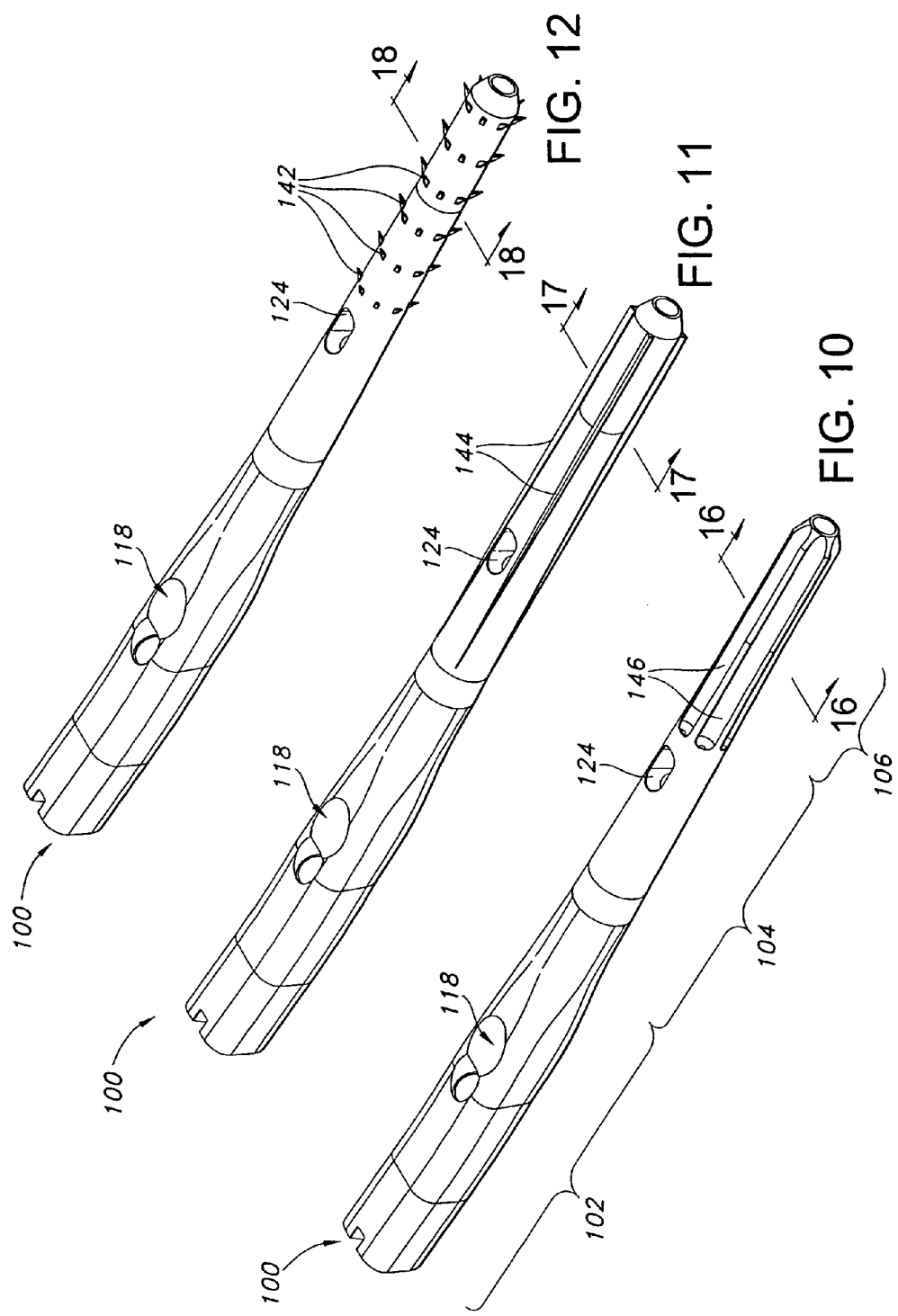

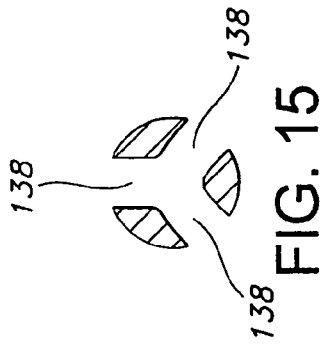
FIG. 15
FIG. 13
FIG. 14
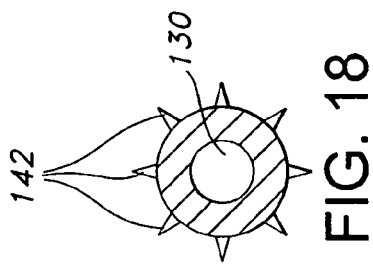
FIG. 18
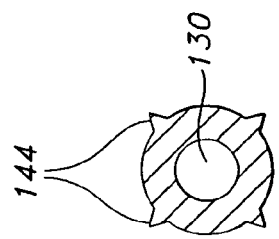
FIG. 17
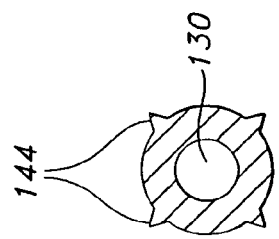
FIG. 16

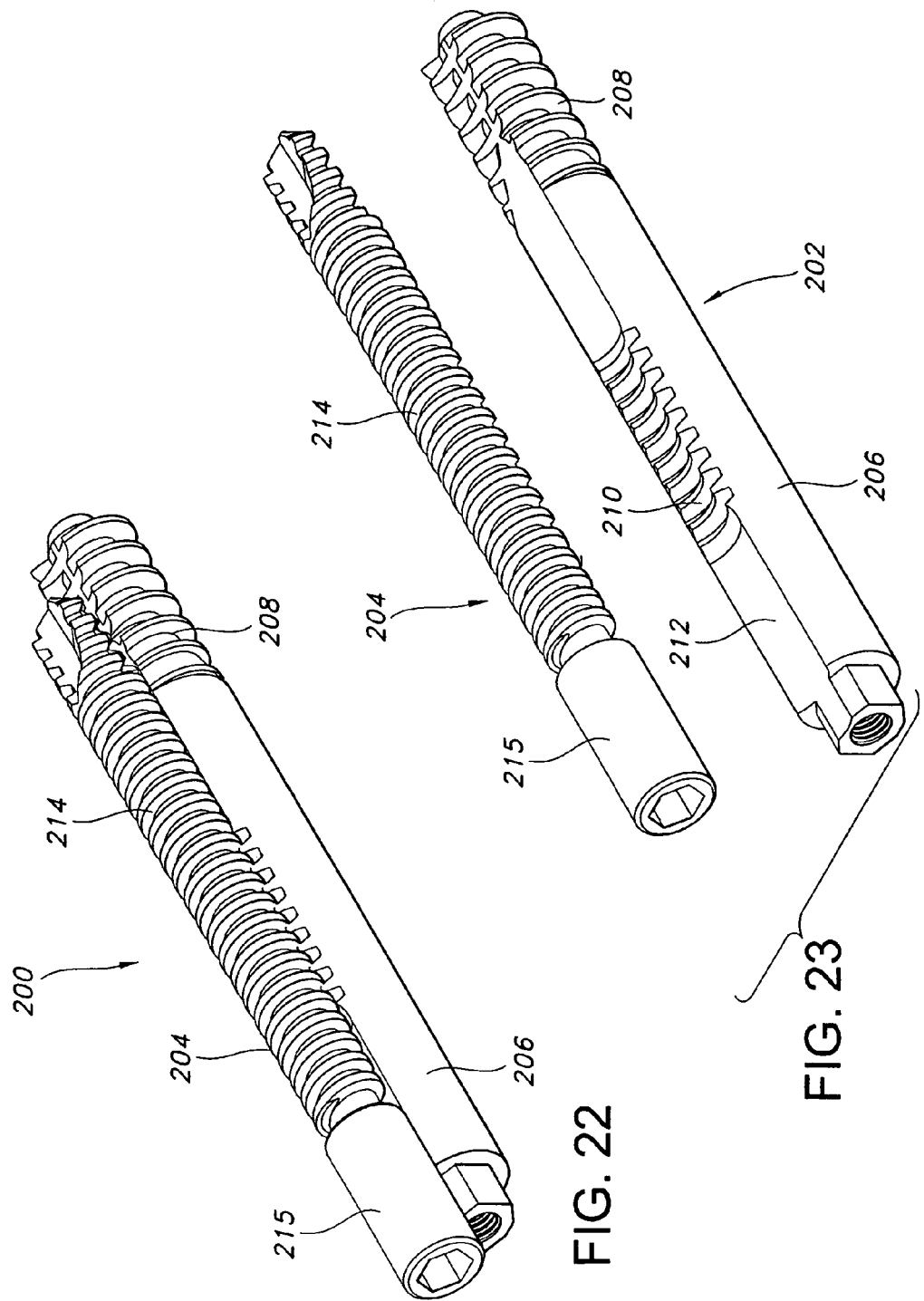

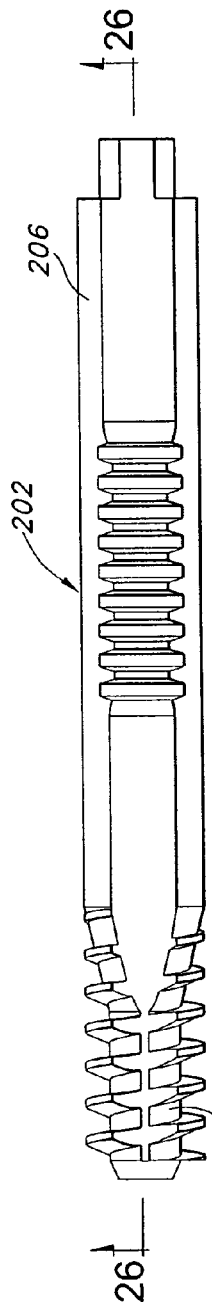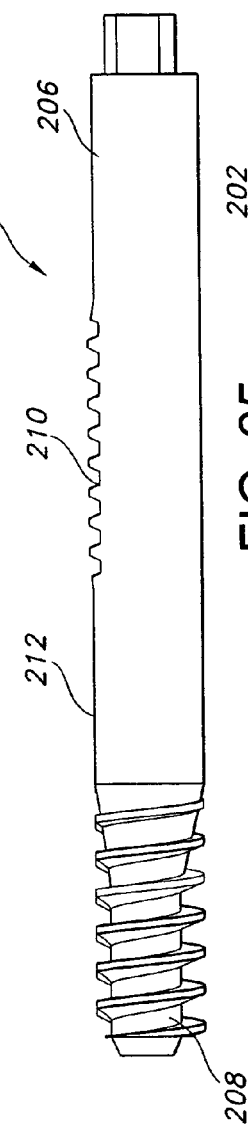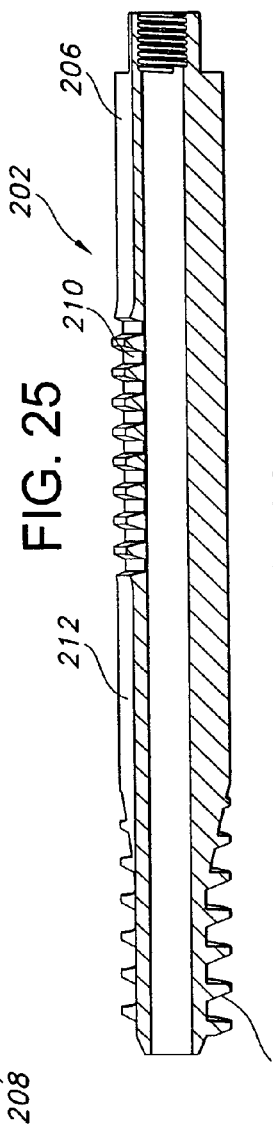

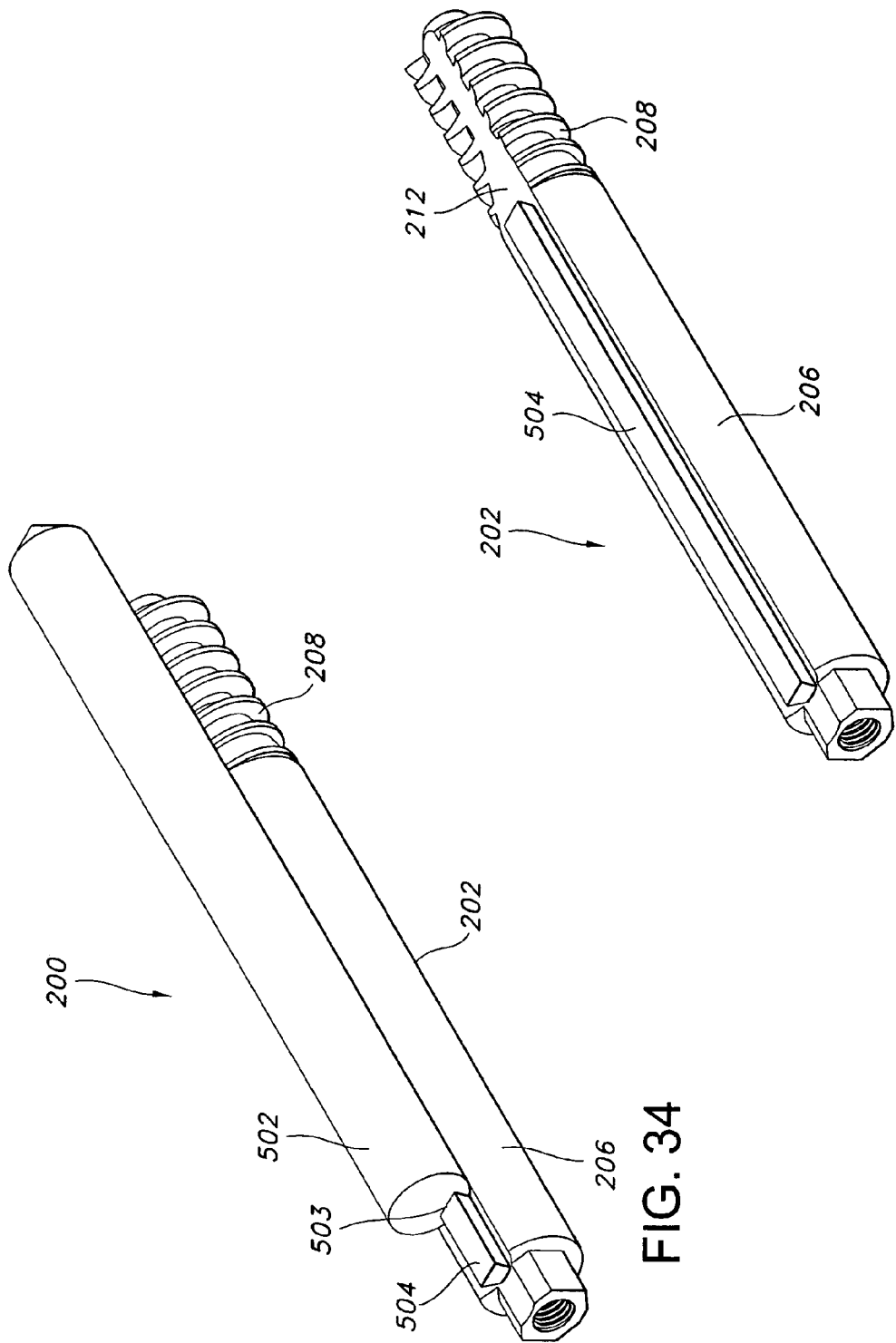

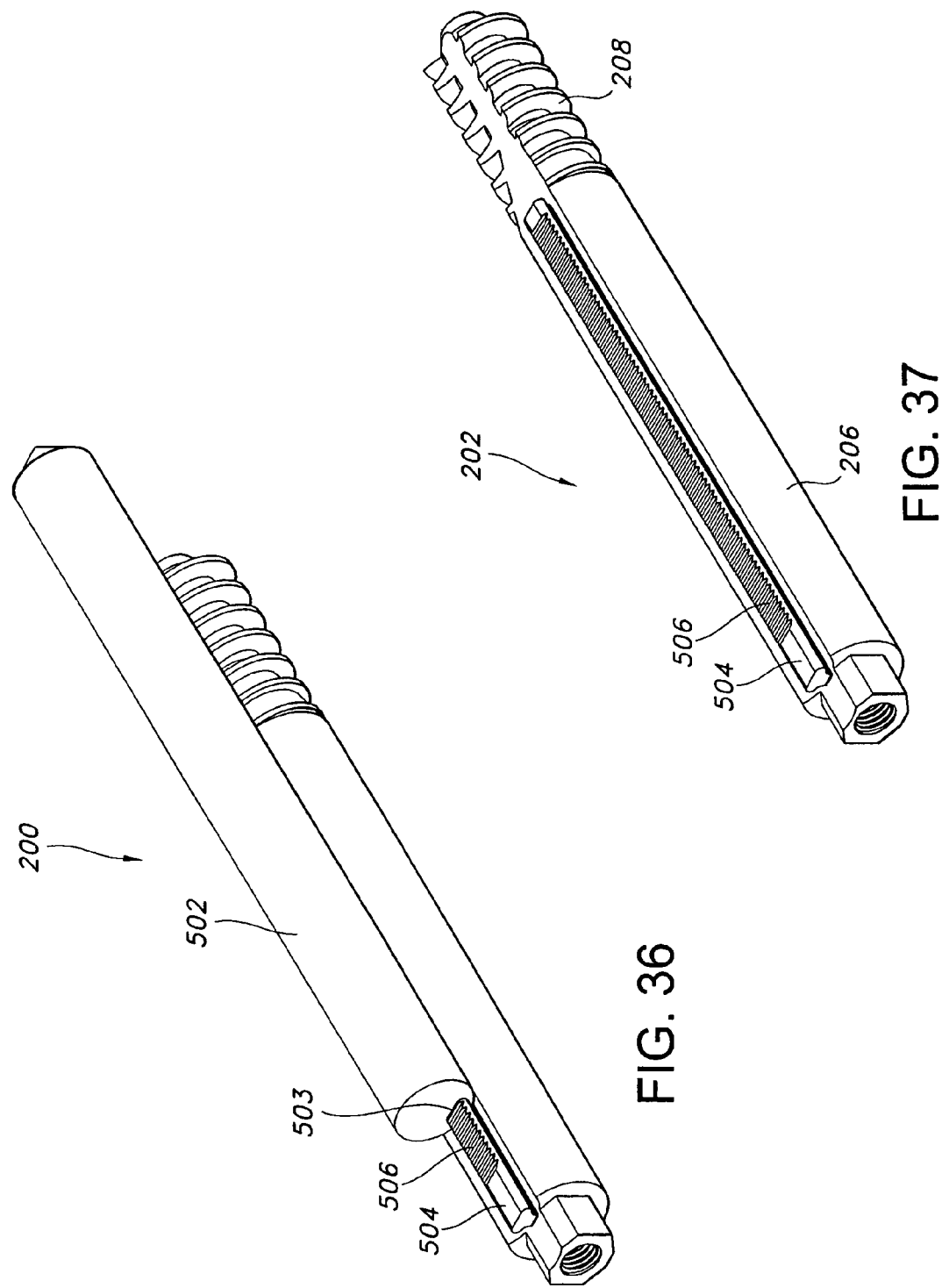

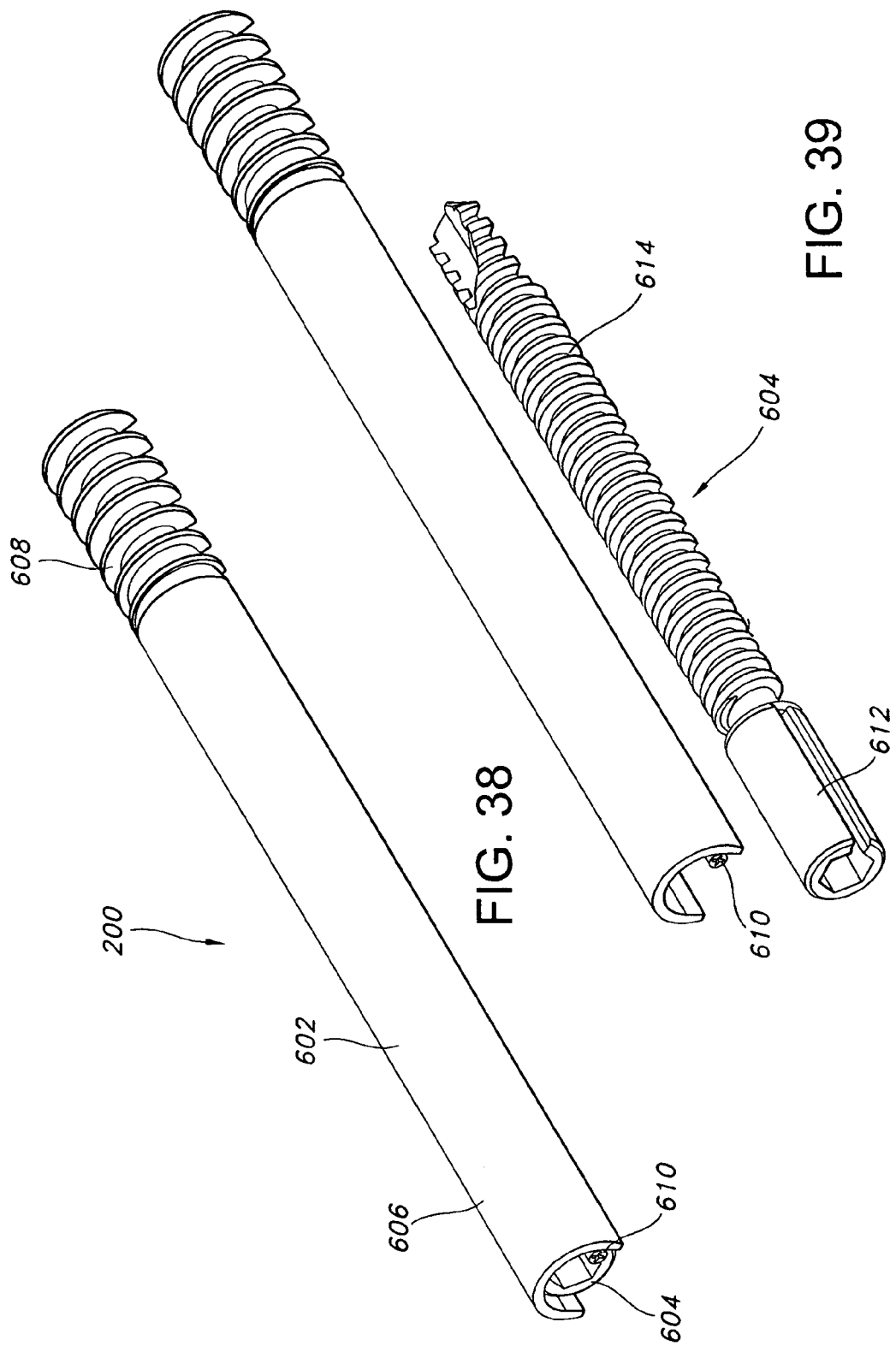

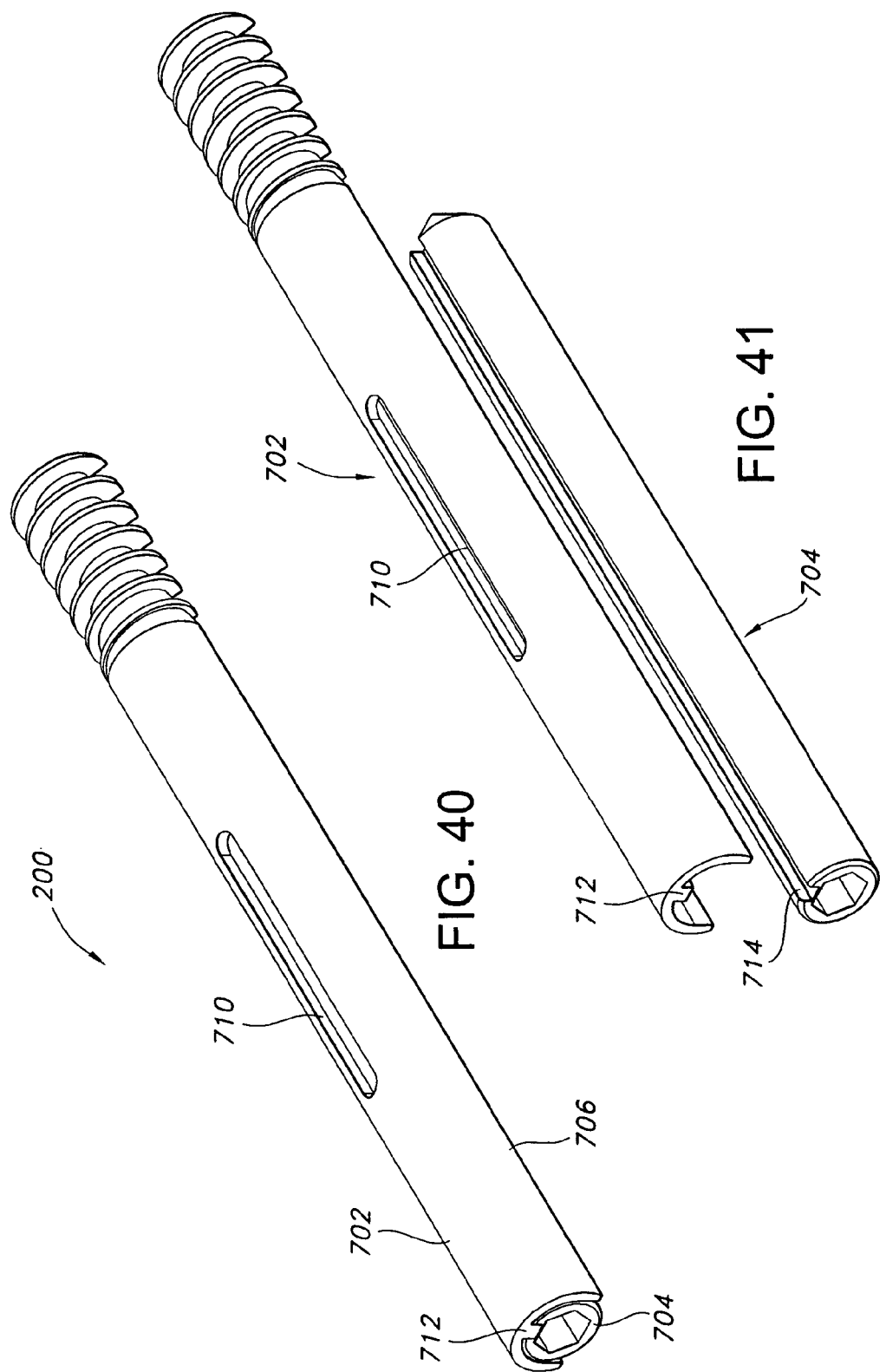

ORTHOPAEDIC IMPLANT AND SCREW ASSEMBLY

CROSS-REFERENCE TO RELATED APPLICATION

This application is a continuation of U.S. Ser. No. 10/658,351 filed Sep. 8, 2003 now abandoned entitled "Orthopaedic Implant and Screw Assembly".

FIELD OF THE INVENTION

The present invention generally relates to a system for coupling bone portions across a fracture and, more specifically, to an intramedullary nail or plate and screw assembly used to treat fractures of long bones such as the femur, humerus and tibia, and various periarticular fractures of these and other bones.

BACKGROUND OF THE INVENTION

There are a variety of devices used to treat fractures of the femur, humerus, tibia, and other long bones. For example, fractures of the femoral neck, head, and intertrochanteric region have been successfully treated with a variety of compression screw assemblies, which include generally a compression plate having a barrel member, a lag screw and a compressing screw. Examples include the AMBI® and CLASSIC™ compression hip screw systems offered by Smith & Nephew, Inc. In such systems, the compression plate is secured to the exterior of the femur, and the barrel member is inserted in a predrilled hole in the direction of the femoral head. The lag screw has a threaded end, or another mechanism for engaging bone, and a smooth portion. The lag screw is inserted through the barrel member so that it extends across the break and into the femoral head. The threaded portion engages the femoral head. The compression screw connects the lag screw to the plate. By adjusting the tension of the compression screw, the compression (reduction) of the fracture can be varied. The smooth portion of the lag screw is free to slide through the barrel member to permit the adjustment of the compression screw. Some assemblies of the prior art use multiple screws to prevent rotation of the lag screw relative to the compression plate and barrel member and also to prevent rotation of the femoral head on the lag screw.

Intramedullary nails in combination with lag screws or other screw assemblies have been successfully used to treat fractures of the femur, humerus, tibia, and other long bones as well. A significant application of such devices has been the treatment of femoral fractures. One such nailing system is the IMHS® system offered by Smith & Nephew, Inc., and covered at least in part by U.S. Pat. No. 5,032,125 and various related international patents. Other seminal patents in the field include U.S. Pat. Nos. 4,827,917, 5,167,663, 5,312,406, and 5,562,666, which are all assigned to Smith & Nephew, Inc. These patents are all hereby incorporated by reference A typical prior art intramedullary nail may have one or more transverse apertures through its distal end to allow distal bone screws or pins to be screwed or otherwise inserted through the femur at the distal end of the intramedullary nail. This is called "locking" and secures the distal end of the intramedullary nail to the femur. In addition, a typical intramedullary nail may have one or more apertures through its proximal end to allow a lag screw assembly to be screwed or otherwise inserted through the proximal end of the intramedullary nail and into the femur. The lag screw is positioned across the break in the femur and an end portion of the lag screw engages the femoral head. An intramedullary nail can also be used to treat shaft fractures of the femur or other long bones.

As with compression hip screw systems, intramedullary nail systems are sometimes designed to allow compression screws and/or lag screws to slide through the nail and thus permit contact between or among the bone fragments. Contact resulting from sliding compression facilitates faster healing in some circumstances. In some systems, two separate screws (or one screw and a separate pin) are used in order, among other things, to prevent rotation of the femoral head relative to the remainder of the femur, to prevent penetration of a single screw beyond the femoral head, and to prevent a single screw from tearing through the femoral neck and head. When an additional screw or pin is used, however, unequal forces applied to the separated screws or pins can cause the separate screws or pins to be pressed against the sides of the holes through which the separate screws or pins are intended to slide. This may result in binding, which reduces the sliding of the screws or pins through the nail. Conversely, a problem can result from excessive compression of the femoral head toward or into the fracture site. In extreme cases, excessive sliding compression may cause the femoral head to be compressed all the way into the trochanteric region of the femur.

Furthermore, overly rigid nails sometimes generate periprosthetic fractures in regions away from a fracture site. Therefore, it is important that intramedullary nails be adequately flexible in comparison to the bones in which they are implanted.

The harder, generally outer portion of a typical bone is referred to as cortical bone. Cortical bone is usually a structurally sound load-bearing material for support of an implant. A cross-section of a long bone that shows the typical anatomical shape of cortical bone generally reveals a non-circular ring of cortical bone which surrounds a medullary canal. Accordingly, the medullary canal generally features a non-circular cross section. Intramedullary nails of the prior art, however, are usually round or square in cross-section, and therefore not anatomically consistent with the cortical bone or the medullary canal. Some have addressed this problem by reaming the medullary canal of the bone with a round reamer in order to cause the nail to fit the cortical bone. This approach, however, can remove significant portions of healthy cortical bone.

The problem of providing an effective load bearing physical relationship between an implant and cortical bone in the proximal femur has been addressed in the art of hip replacement devices. Various hip stems have been developed which feature generally non-circular cross sections along their length, in order better to fit the anatomically shaped cortical bone of the proximal femur and thus more evenly and effectively distribute the load between the stem and the bone. However, none of these hip stems have been incorporated into a nail or configured to accept a screw or screws useful in repairing substantially all of the portions of the treated bone. Instead, hip stems as a general matter have been considered as a device for replacing portions of a long bone, and designed and used for that purpose. For example, the typical application of a hip stem includes completely removing a femoral head and neck, implanting a hip stem, and using the hip stem to support an artificial femoral head.

In summary, and without limitation, the foregoing shows some of the shortcomings of the state of the art in this field. Among other things, what is needed is an orthopaedic implant system that includes a superior sliding screw or other mechanism for applying compression across a fracture. Some embodiments would also provide a sliding screw or other mechanism that obtains adequate bone purchase while reducing the incidence of cut-out, rotational instability, and excessive sliding. An anatomically appropriately shaped implant for achieving improved cortical bone contact would also be advantageous. Where the implant is an intramedullary nail, the nail would provide for reduced reaming and removal of healthy bone. An improved nail may also have a cross-section that provides a greater area of material on the side of the nail that is placed under a greater tensile load when the nail is subjected to a typical bending load. Additionally, an improved implant system could include a sliding screw in combination with intramedullary nails of various designs, or in combination with plates. Combinations of any of these with each other or combinations of each other, and/or with other devices or combinations of them also present opportunities for advancement beyond the state of the art according to certain aspects of the present invention.

SUMMARY OF THE INVENTION

Methods, devices and systems according to certain aspects of this invention allow treatment of bone fractures using one or both of an structure configured to be implanted in or stabilize a first bone fragment and a fastening assembly. The structure may take the form of a plate or other device for at least partial application to the outer surface of bone, or an implant for at least partial implantation within bone. Such implants may include a proximal section having a transverse aperture, and an aperture substantially along their length. Preferably, they include at least one cross-section in their proximal portions which features a shape that imparts additional strength and resistance to tension. Such shapes can be provided, for instance, by one or both (i) adding additional mass in lateral portions of the cross section, and (2) strategically adding and reducing mass in the cross section to take advantage of flange effects similar to the way flanges add structural benefits to I-beams and channels. One way to characterize such cross-sections, which can but need not be asymmetrical with respect to at least one axis, is that they generally feature a moment of inertia extending in a lateral direction from a point that is the midpoint of a line from a lateral tangent to a medial tangent of the cross section. In some structures, that line is coplanar with the axis of the transverse aperture and coplanar with the cross section and thus defined by the intersection of those planes. The endpoints of that line can be defined as the intersection of the line with tangents to the medial aspect and the lateral aspect of the cross section, respectively. Such implants also typically include a distal section and a transition section that provides a coupling between the proximal section and the distal section.

Fastening assemblies of methods, devices and systems according to certain embodiments of the invention preferably include an engaging member and a compression device. The fastening assemblies are adapted to be received in the transverse aperture of the implant in a sliding relationship, so that the fastening assembly is adapted to slide with respect to the transverse aperture, and thus apply compression to a fracture and for any other desired purpose. The engaging member is adapted to gain purchase in a second bone fragment. The engaging member and the compression device are configured so that the compression device interacts with a portion of the implant and also with a portion of the engaging member so that adjustment of the compression device controls sliding of the engaging member relative to the implant and thereby enables controlled movement between the first and second bone fragments. In some embodiments, the compression device at least partially directly contacts the second bone fragment when implanted.

BRIEF DESCRIPTION OF THE DRAWINGS

FIG. 1B is a perspective view of an intramedullary nail according to another embodiment of the present invention.

FIG. 1C is a cross-sectional view of a portion of the nail of FIG. 1B.

FIG. 1D is a perspective view of a intramedullary nail according to another embodiment of the present invention.

FIG. 2 is an elevation view of the intramedullary nail of FIG. 1.

FIG. 3 is a cross-section view of the intramedullary nail of FIG. 2 taken through the line 3-3.

FIG. 4 is a side view of the intramedullary nail of FIG. 2.

FIG. 5 is a cross-section view of the intramedullary nail of FIG. 4 taken through the line 5-5.

FIG. 6 is a cross-section of the intramedullary nail of FIG. 4 taken through the line 6-6.

FIG. 7 is a perspective view of an intramedullary nail according to an alternative embodiment of the invention.

FIG. 8 is a perspective view of an intramedullary nail according to an alternative embodiment of the invention.

FIG. 9 is a perspective view of an intramedullary nail according to an alternative embodiment of the invention.

FIG. 10 is a perspective view of an intramedullary nail according to an alternative embodiment of the invention.

FIG. 11 is a perspective view of an intramedullary nail according to an alternative embodiment of the invention.

FIG. 12 is a perspective view of an intramedullary nail according to an alternative embodiment of the invention.

FIG. 13 is a cross-section view of the intramedullary nail of FIG. 7 taken through line 13-13.

FIG. 14 is a cross-section view of the intramedullary nail of FIG. 8 taken through line 14-14.

FIG. 15 is a cross-section view of the intramedullary nail of FIG. 9 taken through line 15-15.

FIG. 16 is a cross-section view of the intramedullary nail of FIG. 10 taken through line 16-16.

FIG. 17 is a cross-section view of the intramedullary nail of FIG. 11 taken through line 17-17.

FIG. 18 is a cross-section view of the intramedullary nail of FIG. 12 taken through line 18-18.

FIG. 22 is a perspective view of the fastener assembly shown in FIG. 20.

FIG. 23 is an exploded view of the fastener assembly of FIG. 20.

FIG. 24 is an elevation view of the engaging member of the fastener assembly of FIG. 23.

FIG. 25 is a side view of the engaging member of FIG. 24.

FIG. 26 is a cross-section view of the engaging member of FIG. 24 taken through line 26-26.

FIG. 27 is an end view of one end of the engaging member of FIG. 24.

FIG. 28 is an end view of the other end of the engaging member of FIG. 24.

FIG. 34 is a perspective view of a fastener assembly according to another embodiment of the invention.

FIG. 35 is a perspective view of the lag screw of the fastener assembly of FIG. 34.

FIG. 36 is a perspective view of a fastener assembly according to another embodiment of the invention.

FIG. 37 is a perspective view of the lag screw of the fastener assembly of FIG. 36.

FIG. 38 is a perspective view of a fastener assembly according to another embodiment of the invention.

FIG. 39 is an exploded view of the fastener assembly of FIG. 38.

FIG. 40 is a perspective view of a fastener assembly according to another embodiment of the invention.

FIG. 41 is an exploded view of the fastener assembly of FIG. 40.

DETAILED DESCRIPTION

Figure 1:
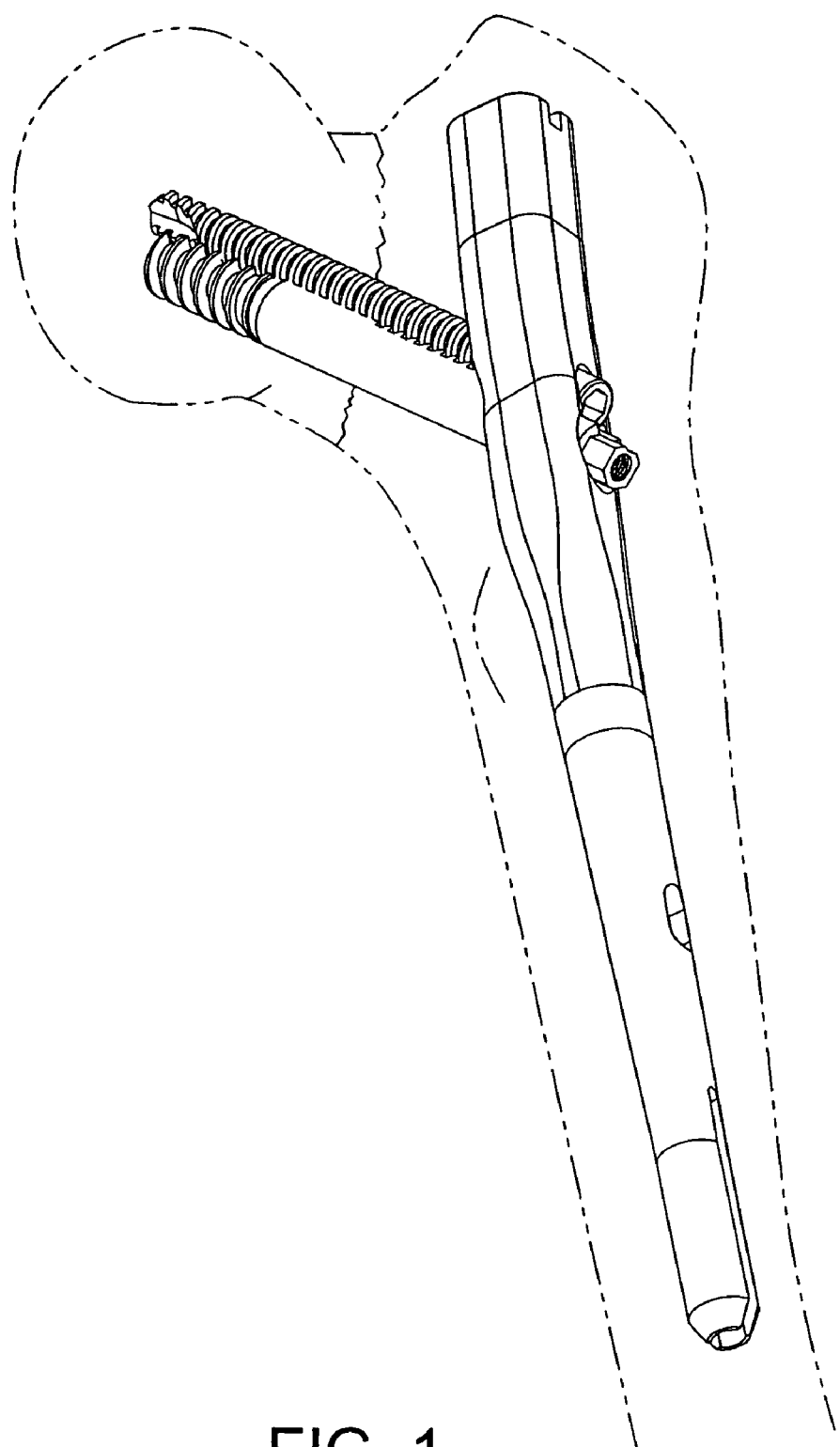
FIG. 1 is a perspective view of an intramedullary nail according to one embodiment of the present invention shown installed in a femur.

Methods, devices and systems according to embodiments of this invention seek to provide improved treatment of femur fractures. FIGS. 1-6 illustrate various views of one embodiment of an intramedullary nail 100 of the present invention. The intramedullary nail 100 has a longitudinal bore 130 throughout to aid in insertion in the bone. The intramedullary nail 100 has a proximal section 102, a transition section 104 and a distal section 106.

The proximal section 102 of the particular structure shown in FIGS. 1-6 preferably features an anatomically inspired shape that corresponds more accurately to typical cortical bone. One version of such shape is shown in the cross-sectional view of the proximal section 102 in FIG. 6. The particular cross-section of the proximal section 102 shown in FIG. 6 is generally non-circular along at least some portions of its length, and has a lateral side or aspect 108 that is larger than a medial side or aspect 109. The lateral side 108 and medial side 109 are joined by a first side 110 and a second side 116. At the intersection of the first side 110 with the lateral side 108 is a first radiused corner 112 and at the intersection of the second side 116 with the lateral side 108 is a second radiused corner 114. The first side 110, second side 116 and lateral side 108 are of approximately equal length. The first side 110 and second side 116 are oriented at acute angles relative to the lateral side 108, so that the medial side 109 is smaller than the lateral side 108. By having the lateral side 108 larger than the medial side 109 the rotational stability of the intramedullary nail 100 is increased, and resistance to bending and twisting can also be enhanced.

The medial side 109 shown in FIG. 6 can be radiused. As can be seen in FIG. 4, the radiused medial side 109 protrudes out from the transition section 104 and continues to the proximal end of the intramedullary nail 100. The protrusion of the medial side 109 corresponds to the calcar region of the femur and improves the evenness of load distribution between the bone and intramedullary nail 100. Furthermore, the general cross-section geometry of the proximal section reduces peak stresses in the proximal section. More specifically, the typical failure mode of an intramedullary nail and screw assembly combination is failure of the nail in tension on its lateral side. The tension is created by bending moment induced by body weight load that is applied to the screw assembly. Therefore, it would be beneficial in reducing stress in the proximal section of a nail to include more material on the side of the nail that is in tension, the lateral side, to shape the cross section more effectively to enhance strength and robustness in the lateral area, or both. The design illustrated in FIG. 6 accomplishes this objective. The lateral side 108 is wider than the medial side 109, thus imparting, at least partially, a flange-like effect. Stress per unit area induced in the material on the lateral side 108 is less than would be the case if the lateral side was featured a smaller cross-sectional area, such as medial side 109.

A structure according to another embodiment of the invention that benefits from the same principle, is shown in FIGS. 1B and 1C which illustrate a intramedullary nail 1100 with a generally circular cross section whose generally circular aperture 1128 is disposed other than concentric with the periphery of the cross section. In the particular structure shown in these two Figures, the offset aperture 1128 is offset toward the medial side 1109 such that a greater portion of material is available to take load, and reduce stress, on the lateral side 1108. Likewise, any cross-section that provides more material on the lateral side of the section reduces stress per unit area in the nail on that side.

Figure 1A:
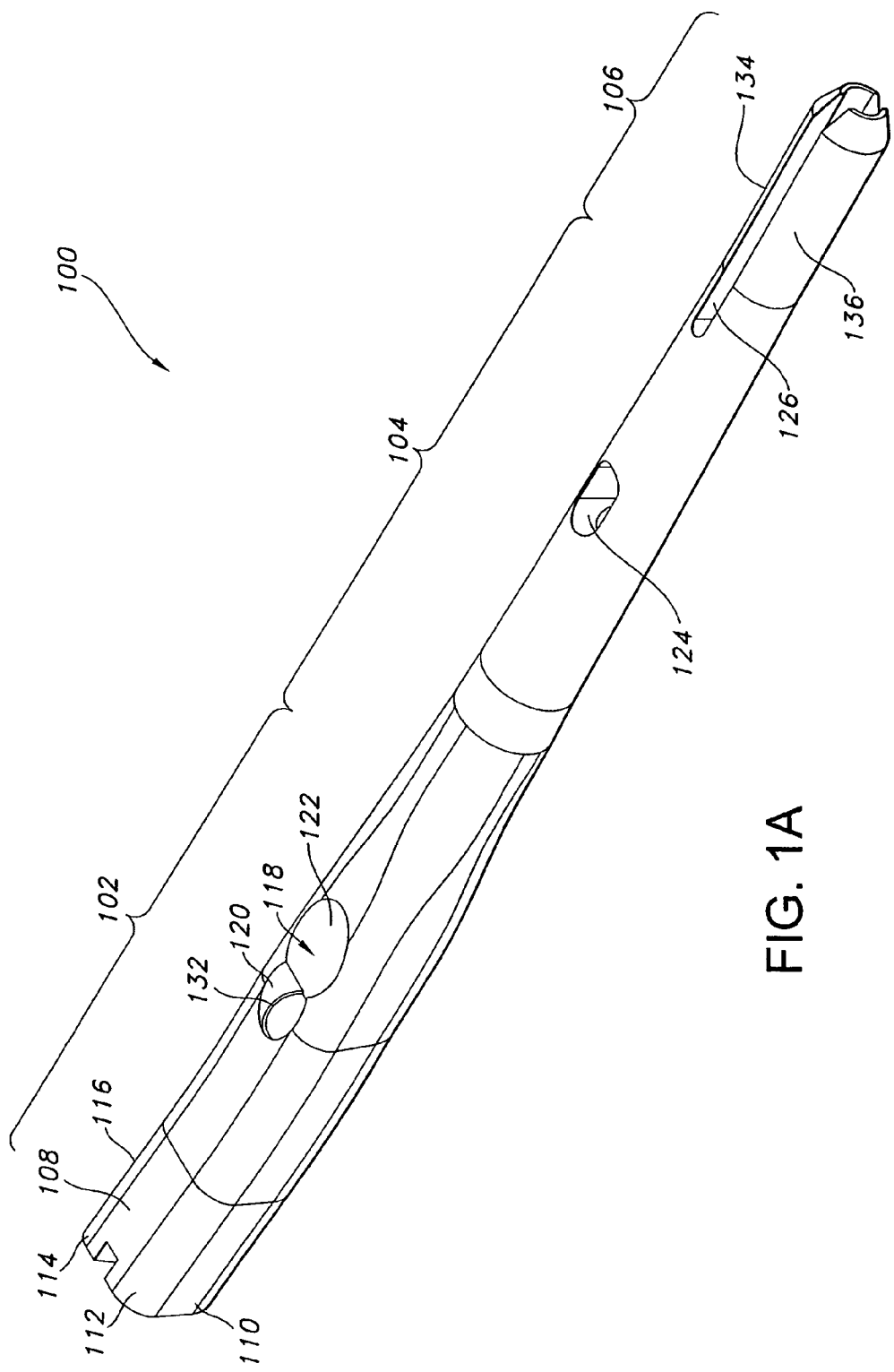
FIG. 1A is a perspective view of an intramedullary nail according to one embodiment of the present invention in greater detail.

Regardless of the particular manner in which material or mass may be added to some portions of the lateral parts of the cross section of proximal portion 102, material may be added and removed from some portions of the cross section in order to increase the strength and robustness of the lateral parts, or both, the effect can be characterized as imparting a moment of inertia to the cross section oriented at least partially in the direction of the lateral side or aspect 108. In a preferred embodiment, the moment of inertia (shown denoted by the letter M on FIG. 6) can be characterized as extending in a lateral direction, or at least partially toward lateral aspect or side 108 from a point P that is the midpoint of a line L extending from the intersection I1 of that line with a tangent T1 to the lateral aspect 108, to the intersection I2 of that line with a tangent T2 to the medial aspect 109. Stated another way, the effect in at least some cases is to create a cross section that features a moment of inertia extending in at least partially lateral direction from a center of the cross section. Preferably, that center can be a midpoint between the lateral and medial edges of the cross section. Alternatively, that center can be the center of mass of the cross section. The radius of gyration reflected by the moment of inertia, which is a function of the square of the distance of the incremental mass from the center, reflects additional strength in lateral parts of the proximal portion 102 caused by more mass or more strategically placed mass in the cross section. In some structures, line L is coplanar with the axis of the transverse aperture and coplanar with the cross section and thus defined by the intersection of those planes. As FIGS. 1A, on the one hand, and 1B and 1C on the other hand reflect, and bearing in mind that these are only two of a myriad of structures that can impart such lateral additional strength and robustness, the cross section can but need not be asymmetrical with respect to at least one of its axes. Additionally, the longitudinal opening 130 can be located to share its central axis with that of the cross section, or it can be offset in order to help impart the lateral strength or for other purposes.

In the particular device shown in FIGS. 1-6, the first side 110, second side 116 and lateral side 108 are flat. Alternatively, these sides could be radiused or otherwise not flat. In the embodiment shown in FIGS. 1-6, the medial side 109 is radiused, but as one skilled in the art could appreciate, the medial side could be flat.

Figure 33:
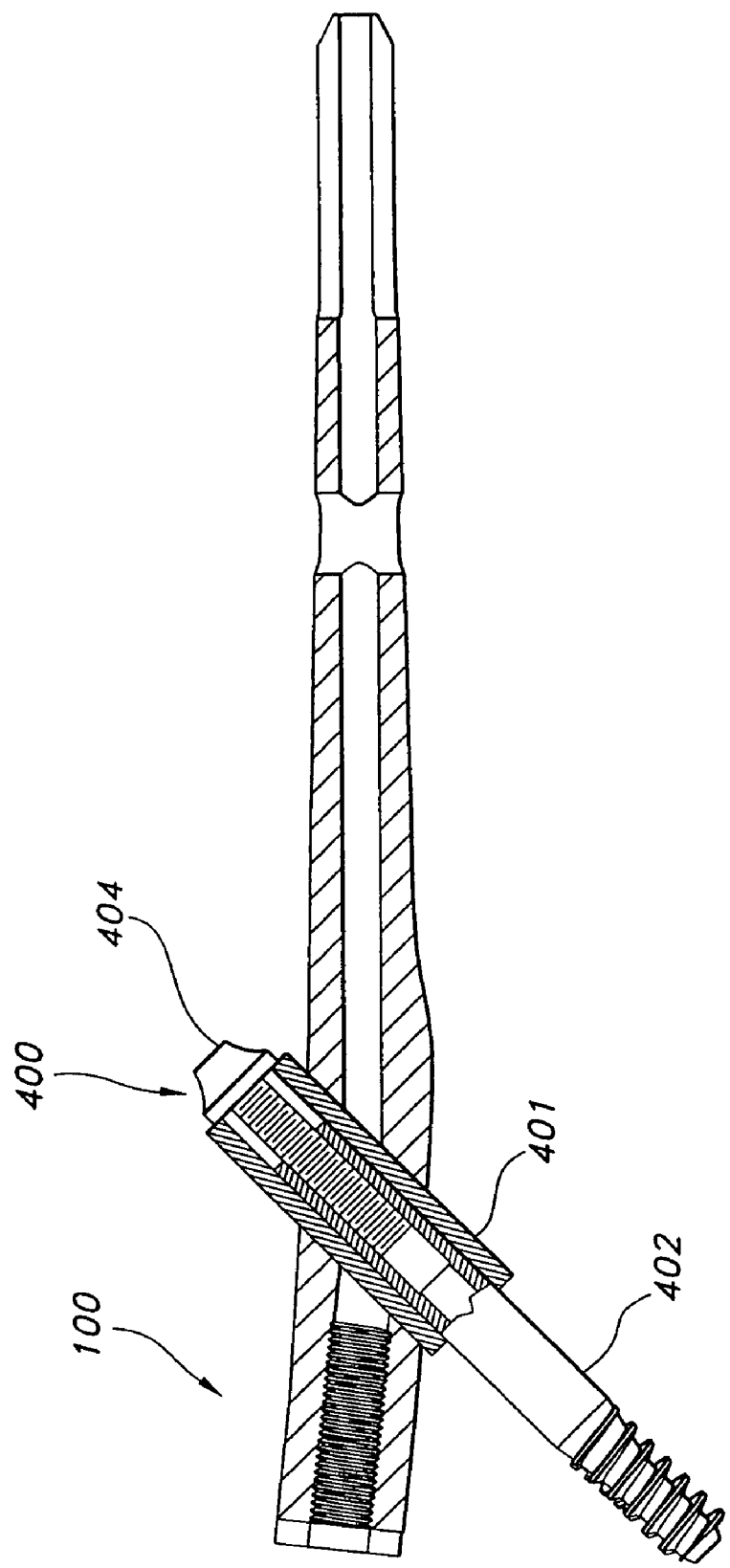
FIG. 33 is a cross-section view of an intramedullary nail and screw assembly according to another embodiment of the present invention.

The proximal section 102 has a transverse aperture 118 that receives a fastening or screw assembly 200 (various versions of which are shown in FIGS. 19-41) through the intramedullary nail 100. One embodiment of the proximal transverse aperture 118, shown in FIGS. 1-4, is formed from two overlapping circular apertures 120, 122, where the proximal circle aperture 120 is smaller in diameter than the distal circle aperture 122. The proximal circle aperture 120 shown has a shoulder 132 for constraining the insertion depth of the screw assembly as will be explained in more detail below. Various other apertures allowing insertion of various screw assemblies could be used as would be known to those skilled in the art. For example, FIG. 33 illustrates the intramedullary nail with a circular aperture. The embodiment of FIG. 33 is described in greater detail below.

The proximal section 102 illustrated in FIG. 3 has a proximal end aperture 128. The proximal end aperture 128 is threaded to allow for the insertion of a set screw that can be used to fix the rotational and sliding position of a screw assembly. A set screw may also include mechanisms for spanning a compression screw 204 and interfering with a lag screw 202 to independently restrict the rotation or sliding of the lag screw 202.

As shown in FIGS. 1-6, the transition section 104 is tapered from the proximal section 102 to the distal section 106. The tapered nature of the transition section 104 creates a press fit in the intramedullary canal that controls subsidence. The tapered transition section 104 assists in preventing the nail 100 from being pressed further down into the intramedullary canal of the femur than intended.

In the embodiment of the intramedullary nail 100 shown in FIGS. 1-6, the cross-section of the transition section 104 is circular, but the cross-section could vary as known to those skilled in the art. The cross-section could be anatomically derived, similar to the cross-section of the proximal section 102, oval or non-circular. In the embodiment shown in FIGS. 1-6, the transition section 104 contains a distal transverse aperture 124. The distal aperture 124 allows the insertion through the intramedullary nail 100 of a distal locking screw for locking of the intramedullary nail 100.

The distal section 106 of the intramedullary nail 100 is generally cylindrical and is configured to provide a reduced bending stiffness. The embodiment shown in FIGS. 1-5 has a longitudinal slot 126 through the center of the distal section 106 that forms two sides 134, 136. The slot reduces bending stiffness at the distal end of the intramedullary nail 100 and reduces the chances of periprosthetic fractures.

FIG. 1D shows an intramedullary nail 100 according to another embodiment of the invention. This nail features, in its proximal portions, a noncircular cross section that is symmetrical with respect to its lateral—medial axis (in this case, preferably but not necessarily, oval shaped in cross-section), and which features a centered longitudinal bore (in this case, preferably but not necessarily, circular in cross-section). This nail achieves additional stability to the extent it resists twisting in the medullary canal. It also accomplishes the aim of placing more mass toward the lateral edge or aspect of the proximal cross section. Furthermore, it places additional mass toward the medial edge or aspect, and thus provides additional structure that acts as a fulcrum to decrease the mechanical advantage of the fastening assembly which when loaded is the component that imposes tensional stress on the lateral edge or aspect.

FIGS. 7-18 illustrate intramedullary nails 100 according to other embodiments of the invention. FIGS. 7 and 13 illustrate an intramedullary nail 100 having no longitudinal bore throughout.

FIGS. 8 and 14 illustrate an intramedullary nail 100 having stiffness reduction slots 140 in the transition section 104 and the distal section 106. The stiffness reduction slots 140 reduce the bending stiffness at the distal end of the intramedullary nail 100 and could be used to receive locking screws in some embodiments.

FIGS. 9 and 15 illustrate an intramedullary nail 100 having three longitudinal slots 138 in the distal section 106 and a portion of the transition section 104 forming a cloverleaf pattern. This pattern more readily permits blood flow near the intramedullary nail 100 and also reduces bending stiffness at the distal end of the nail 100.

FIGS. 10 and 16 illustrate an intramedullary nail 100 in which the distal section 106 and a portion of the transition section 104 have a series of longitudinal grooves 146. The longitudinal grooves 146 reduce bending stiffness at the distal end, provide rotational resistance, and enhance blood flow near the intramedullary nail 100.

FIGS. 11 and 17 illustrate an intramedullary nail 100 where the transition section 104 and the distal section 106 have fins 144. The fins 144 provide rotational resistance for the intramedullary nail 100.

FIGS. 12 and 18 illustrate an intramedullary nail 100 having barbs 142 located on the distal section 106 and a portion of the transition section 104. The barbs 142 provide rotational resistance for the intramedullary nail 100.

Intramedullary nails according to the present invention may be inserted into a patient by any suitable known technique. Generally, the intramedullary canal of the bone is prepared with an appropriate tool to create a void for insertion of the nail. Some portions of the void may be prepared to be about 1 millimeter larger than the perimeter of the nail to permit sufficient space for blood flow after insertion of the nail. A guide pin or wire is optionally inserted into the prepared medullary canal. The nail is then introduced into the desired position. If the nail is cannulated, the nail can be introduced over the guide wire. The position of the nail may be confirmed by image intensification.

Figure 19:
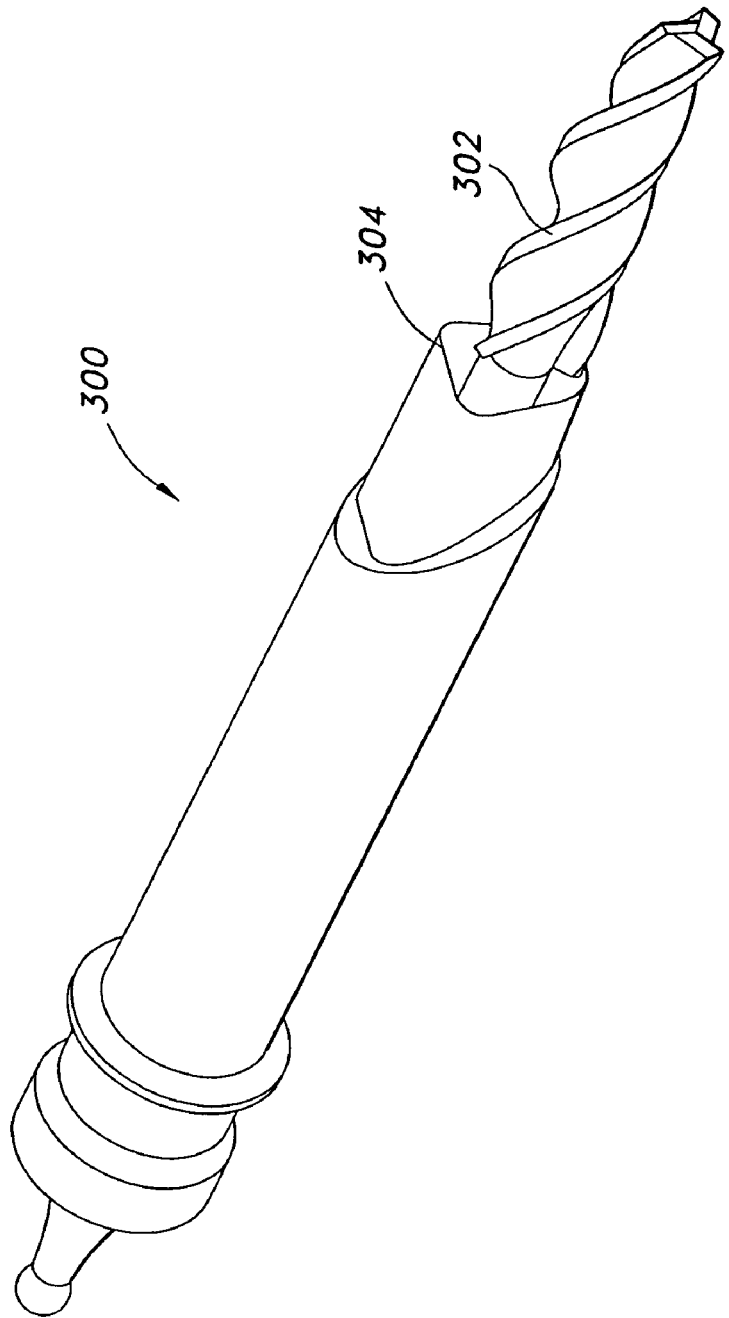
FIG. 19 is a perspective view of a tool according to an embodiment of the present invention for preparing bone to receive certain devices according to certain embodiments of the present invention.

FIG. 19 shows one embodiment of a tool 300 for preparing a medullary canal. The tool has a drill bit 302 for reaming and also a mortise chisel 304. In operation, the drill bit 302 reams out the medullary canal of the femur and the mortise chisel 304 cuts out a larger section in the more proximal end of a bone. As shown in FIG. 19, the mortise chisel 304 has an anatomically derived cross-section of approximately the same shape as the proximal section of the intramedullary nail. By applying this type of shaped, mortise chisel, the proximal end of the nail will be better enabled to seat on cortical bone that has been only minimally altered. The mortise chisel 304 may be of a wide variety of shapes, even complicated, asymmetrical shapes. This is advantageous because it enables a device and method for preparing voids able to accept a wide variety of shapes of intramedullary nails without merely over-reaming circular voids. Preparation of an accurately conforming void is valuable in avoiding unnecessary removal of healthy bone, and in ensuring stable seating of the nail.

In operation, the tool 300 of the embodiment shown is advanced as a unit, with the drill bit 302 reaming and the mortise chisel 304 cutting simultaneously. The drill bit 302 may be turned with a power driver, or by hand. Likewise, the entire tool 300 may be advanced into a medullary canal manually, or advanced with the assistance of mechanical advantage or power equipment. In other configurations, the drill bit 302 may be cannulated (not shown) such that the entire tool 300 is operable over and guided by a guide wire that has been inserted into the medullary canal.

In other embodiments, the bit for reaming is a more traditional reamer that is separate from a cutting tool such as the mortise chisel 304. The method for preparing a void in such an instance would include first reaming an opening with a traditional reamer. A device such as a chisel or a broach, shaped similar to the intramedullary nail to be implanted, would then be used to prepare the void. The chisel or broach may be driven in by hand, with the assistance of a hammer or mallet, or with the use of other power equipment. A nail consistent with the void prepared would then be implanted.

Other custom instruments such as a contoured broach or a custom router bit and template could be used as well. Broaches have long been used to prepare openings for hip stems, and the use of a broach would be familiar to one of skill in the art. A router bit and template could be use, in effect, to mill out the desired shape in the bone. Such a method might also be used in combination with reaming or broaching to create the desired void.

The intramedullary nail of the present invention can be used to treat proximal femoral fractures and femoral shaft fractures, among other fractures of long bones. When used to treat femoral shaft fractures, the intramedullary nail is secured in the femur by one or more fastening devices. When used for the treatment of proximal femoral fractures the intramedullary nail is preferably used in conjunction with a proximal screw assembly.

Figure 20:
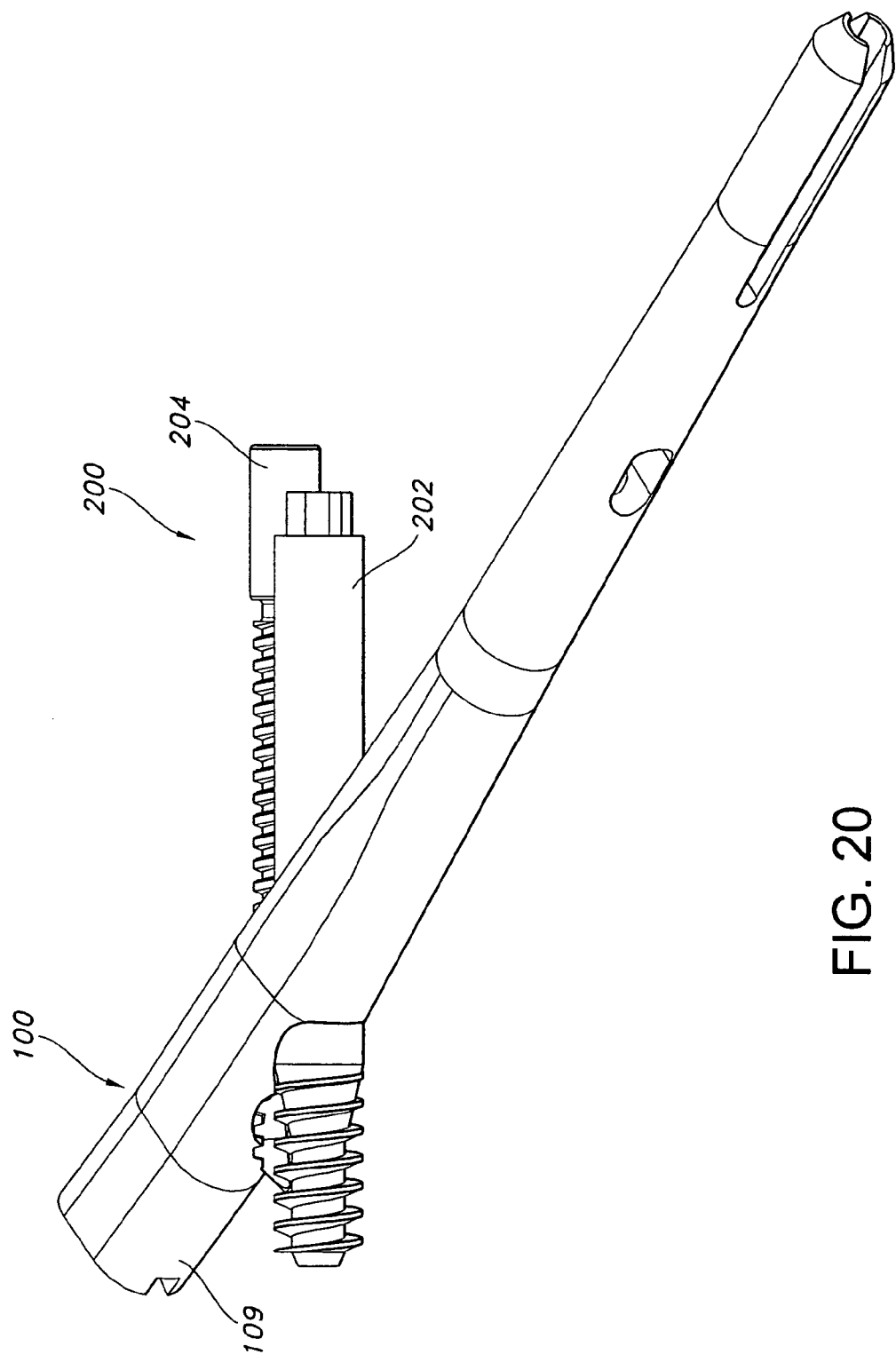
FIG. 20 is a perspective view of a device which includes a version of a fastener assembly according to one embodiment of the present invention.
Figure 21:
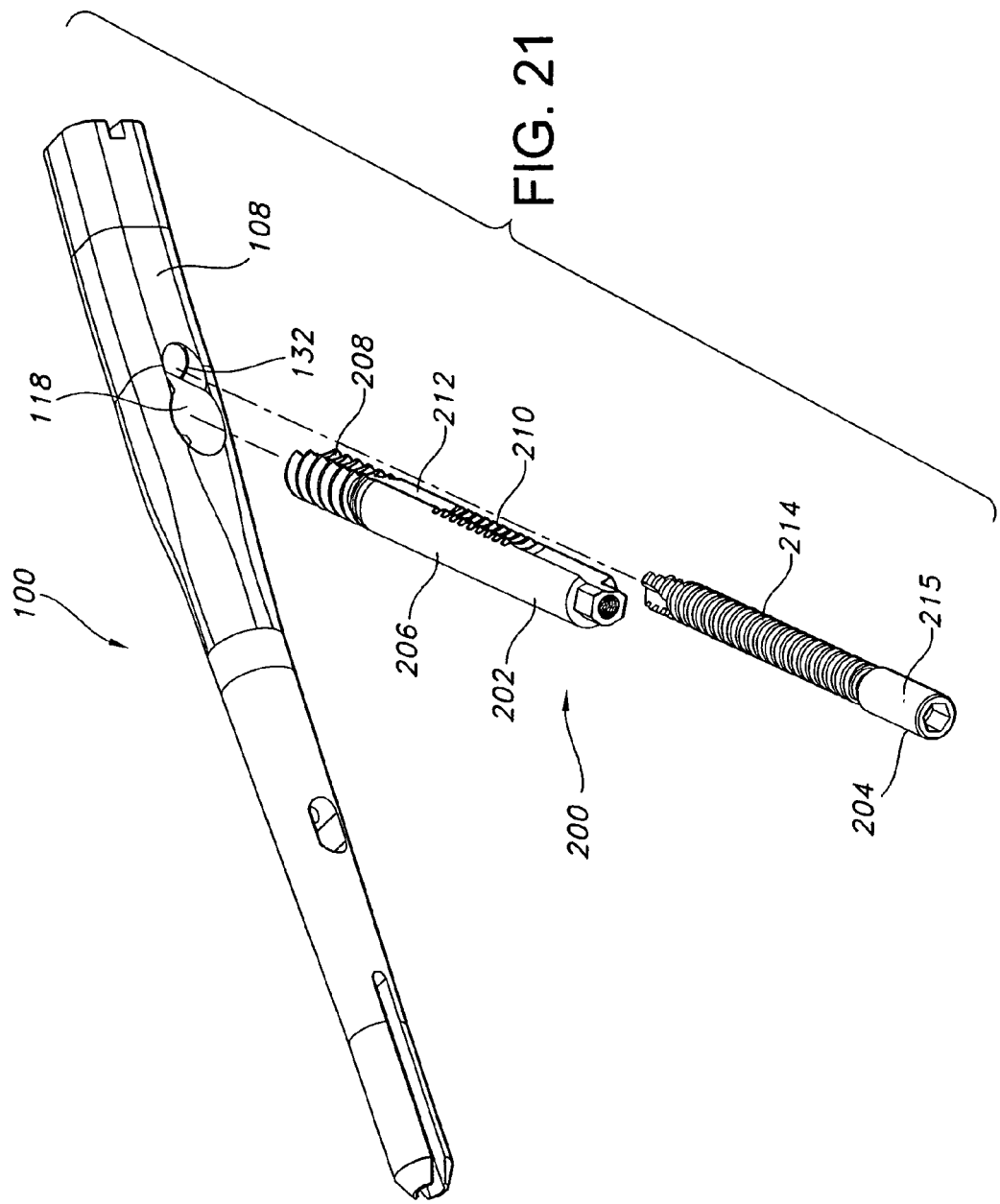
FIG. 21 is an exploded view of the intramedullary device and fastener assembly shown in FIG. 20.
Figure 29:
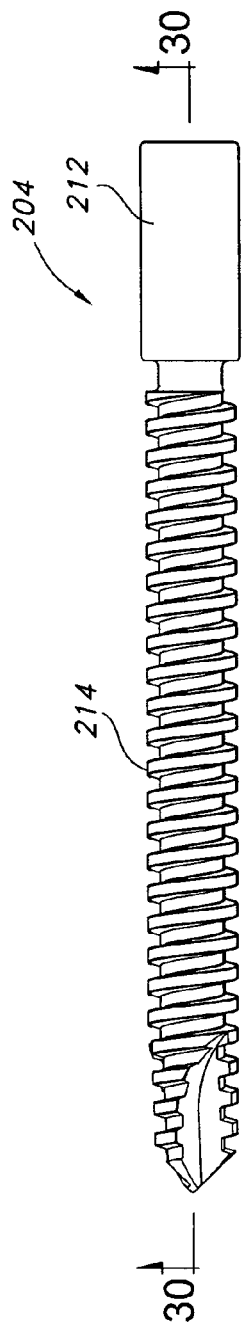
FIG. 29 is an elevation view of the compression device of the fastener assembly of FIG. 22.
Figure 30:
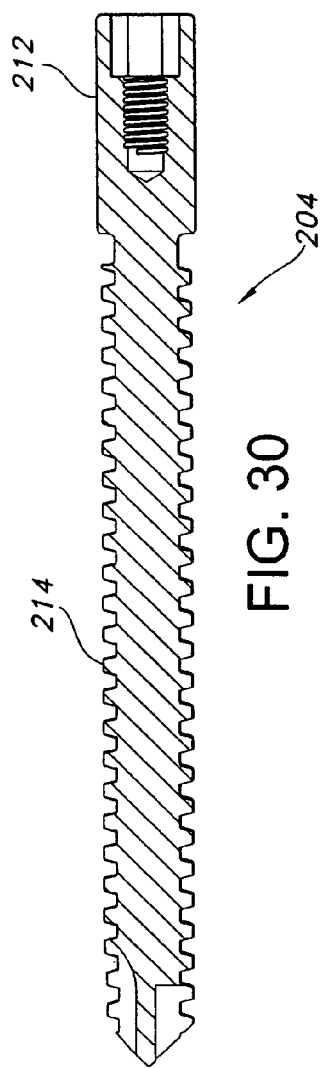
FIG. 30 is a cross-section view of the compression device of FIG. 29 shown through line 30-30.
Figure 31:
FIG. 31 is an end view of one end of the compression device of FIG. 29.
Figure 32:
FIG. 32 is an end view of the other end of the compression device of FIG. 29.

FIGS. 20 and 21 illustrate an intramedullary nail 100 according to one embodiment of the present invention used in conjunction with a fastener assembly 200 according to one embodiment of the present invention. This type of fastener assembly may be used in various other bones and to treat a number of other indications, but for the purpose of providing an example, it is being described here in use with the proximal femur. In general, the screw assembly is useful in any situation where one fragment of a bone is to be drawn back toward or pushed away from another fragment of the bone in a controlled manner. The fastener assembly provides the additional advantage of being configurable to allow sliding of the assembly in a desired direction after the movement of the bone fragments has been accomplished.

As shown in FIG. 21, the axis of the proximal transverse aperture 118 in the intramedullary nail 100 is angled relative to the proximal section 102 and in use, is directed towards the femoral head. In this embodiment of the fastener assembly 200, an engaging member such as a lag screw 202 is used in conjunction with a compression device, such as a compression screw 204 or a compression peg. The screws are configured such that when in use the circumference of the lag screw 202 partially intersects with the circumference of the compression screw 204, so that the compression screw 204 nests partially within the circumference of the lag screw 202. This particular combination of lag screw 202 and compression screw 204 are further illustrated in FIGS. 22 through 32. Briefly, the lag screw 202 shown in these figures is intended to engage the femoral head and to slide in the transverse aperture 118 of the nail 100. The compression screw 204 engages a shoulder or other structure in nail 100's transverse aperture 118 and also threads in the portion of lag screw 202 within which compression screw 204 nests, so that rotation of compression screw 204 controls sliding of the lag screw 202 relative to the nail 100 and thus compression of the femoral head against the fracture site.

The lag screw 202 shown in these drawings includes an elongate body 206 and threaded end 208. As shown in FIGS. 24 and 25, the threaded end 208 does not include a sharp end, which reduces the possibility of the cut out through the femoral head. The elongate body 206 includes a channel 212 that allows for the positioning of the compression screw 204 partially inside the circumference of the lag screw 202. In the embodiment shown in FIGS. 21-23, the engaging member has an external channel on an elongate surface of the engaging member. The channel 212 includes a threaded portion 210 that compliments and cooperates with a threaded section 214 of the compression screw 204. The compression screw 204 includes a threaded section 214 and a head section 215 The threaded section 214 of the compression screw 204 is configured such that the threads are relatively flat and smooth at the exterior surface so that they can easily slide in the aperture and also reduce the possibility of cut out.

The lag screw 202 is received in the proximal transverse aperture 118 and into a pre-drilled hole in the femur so that the lag screw 202 extends across the break and into the femoral head. The threaded end 208 of the lag screw 202 engages the femoral head as the lag screw 202 is rotated within aperture 118 causing its threaded end 208 to engage the femoral head. The threaded end 208 may be any device for obtaining purchase in the femoral head, and includes but is not limited to, threads of any desired configuration including helices, barbs, blades, hooks, expanding devices, and the like. The placement depth of the lag screw 202 into the femoral head differs depending on the desired compression of the fracture.

The compression screw 204 can also be received through the proximal transverse aperture 118 into a predrilled hole in the femoral head. The threaded section 214 of the compression screw 204 engages with the threaded portion of the channel 212 of the lag screw 202. The proximal transverse aperture 118 has an interior shoulder 132 (FIG. 21) to limit the sliding of the compression screw 204 in the general medial direction and, therefore, the lag screw 202, through the aperture 118. When the compression screw 204 is tightened, the compression screw threads 214 engage with the lag screw channel threaded portion 210 and the compression screw 204 moves in the generally medial direction down the lag screw 202. The head section 215 of the compression screw 204 engages the shoulder 132 of the proximal transverse aperture 118 preventing the compression screw 204 from moving further in the general medial direction. As the compression screw 204 is tightened, the lag screw 202 is drawn in the general lateral direction toward the intramedullary nail providing compression to the fracture. The compression screw 204 partially intersecting the circumference of the lag screw 202 provides greater surface resistance and aids in the prevention of femoral head rotation. The compression screw 204 therefore acts not only as a part of the mechanism for moving fragments of the fractured bone relative to one another, but also directly contacts bone of the femoral head to help prevent the femoral head from rotating about the axis of the lag screw 202.

In one embodiment, a set screw (not shown), positioned in the proximal end aperture 128 of the intramedullary nail, is used to engage the compression screw 204 and fix the compression screw 204 and lag screw 202 in place. The use of the set screw to fix the fastener assembly 200 in place is fracture pattern dependent. If a set screw is not used to engage the fastener assembly, the fastener assembly 200 can slide within the proximal aperture limited by the shoulder 132.

In the embodiment of the lag screw and compression screw shown in FIGS. 20-32, the diameter of the compression screw 204 is smaller than the diameter of the lag screw 202. The diameters of the lag screw and compression screw could be the same or the diameter of the lag screw could be smaller than the diameter of the compression screw. The threads of the lag screw and the compression screw could be a variety of different shapes as known to those skilled in the art. In general, the purpose of the lag screw is to obtain purchase in bone, and the purpose of the compression screw is to engage with and draw or move the lag screw. Any configuration that permits these functions is within the scope of the invention.

The fastener assembly could additionally be configured to allow the addition of a prosthetic femoral head and neck. In such an embodiment, the lag screw 202 would be replaced with a prosthetic head and neck. The neck would fit into the proximal transverse aperture 118 in the nail 100. The design would be beneficial where degeneration or re-injury of a repaired femoral fracture and hip joint later necessitated a total hip arthroplasty (THA). The decision to accomplish a THA could be made interoperatively, or after some period of time. Instead of having to prepare a femur to accept a hip stem as is known in association with THA, only a small portion of bone would need to be removed, along with the fastener assembly 200. The prosthetic head and neck could then be inserted into the proximal transverse aperture 118, the acetabulum prepared, and the remainder of the THA completed.

FIG. 33 is a cross-section view of an intramedullary nail 100 according to another embodiment of the invention with an alternate fastener assembly 400. The fastener assembly illustrated is very similar to the compressing fastener assembly of Smith & Nephew's IMHS® system, as is more thoroughly disclosed in U.S. Pat. No. 5,032,125, which is hereby incorporated by reference, and various related international patents. The improvement of the device illustrated is that it includes the intramedullary nail 100 with an anatomically derived shape and its multiple advantages as discussed above. In operation, a sleeve 401 fits through the intramedullary nail 100, and may be secured to the nail by set screw, or other effective mechanisms. A sliding lag screw 402 is able to move axially within the sleeve 401. A compressing screw 404 is threaded into the sliding lag screw 402 such that tightening of the compressing screw 404 draws the sliding lag screw 402 back into the sleeve 401. With this mechanism, a bone fragment may be brought into a desired position, but still permitted to achieve sliding compression once positioned.

FIGS. 34-35 illustrate a fastener assembly 200 according to another embodiment of the invention having a lag screw 202 and a compression peg 502. As shown in FIG. 34, the lag screw 202 and the compression peg 502 are configured such that, when in use, the circumference of the lag screw 202 partially intersects with the circumference of the compression peg 502, although in some embodiments the circumferences might be adjacent rather than intersecting. The lag screw 202 includes an elongate body 206 and threaded end 208. The lag screw 202 has a key 504 on the channel 212. The compression peg 502 has a slot 503 that is adapted to receive the key 504 of the lag screw 202. The key 504 and slot 503 can be a variety of complimentary shapes, such as, when considered in cross section, triangular, D-shaped, key-holed and other shapes as are apparent to those skilled in the art. In operation, the compression peg 502 may be moved relative to the lag screw 202 by a compression tool (not shown) that applies disparate forces between the compression peg 502 and the lag screw 202, or between the entire assembly and the intramedullary nail 100.

In the fastener assembly 200 shown in FIGS. 34-35, the lag screw 202 is received to slide in a proximal aperture of the intramedullary nail so that the lag screw 202 extends across the break and into the femoral head. The threaded end 208 of the lag screw 202 engages the femoral head. Once the lag screw 200 has been properly engaged with the femoral head, the compression peg 502 is inserted in the proximal aperture into a predrilled hole in the femoral head, in order to prevent further rotation of the lag screw 202 as the slot 503 of the compression peg 502 receives the key 504 of the lag screw 202. By providing more area for resistance, the compression peg 502 helps to prevent the rotation of the femoral head on the lag screw 202. The compression peg 502 is fixed in position in the intramedullary nail 100 by a set screw positioned in the proximal end aperture of the nail. The lag screw 202 can slide on the compression peg 502 through the proximal aperture. In another embodiment, the compression peg 502 has barbs on its surface.

A fastener assembly 200 according to another embodiment of the invention is illustrated in FIGS. 36-37. The fastener assembly 200 of this embodiment has a compression peg 502 and a lag screw 202 similar to the embodiment illustrated in FIGS. 34-35 except that the key 504 of the lag screw 202 and the slot 503 of the compression peg 502 have complimentary ratchet teeth 506. The compression peg 502 is fixed in position in the intramedullary nail by a set screw positioned in the proximal end aperture. Compression of the fracture can be achieved by pulling the lag screw in the general lateral direction. The ratchet teeth 506 allow the lag screw 202 to move in the general lateral direction, but prevent the lag screw 202 from moving in the general medial direction. A compression tool similar to the tool describe in association with FIGS. 34-35 may be used to accomplish the movement.

FIGS. 38-39 a fastener assembly 200 according to another embodiment of the invention having a lag screw 602, a cross hair screw 610 and a compression screw 604. The lag screw 602 includes an elongate body 606 and threaded end 608. The elongate body 606 is semi-circular shaped in cross section. The screws 602, 604, 610 are configured so that the circumference of the lag screw 602 intersects with the circumferences of the cross hair screw 610 and the compression screw 604. The elongate body 606 of the lag screw 602 is threaded to compliment and cooperate with a threaded section 602 of the cross hair screw 610. The cross hair screw 610 is threaded to engage with the lag screw 602 and the compression screw 604. The compression screw 604 includes a threaded portion 614 and a head portion 612.

In this embodiment, the lag screw 602, the cross hair screw 610 and the compression screw 604 are received simultaneously to slide in a proximal aperture of an intramedullary screw. The lag screw 602 extends across the break and into the femoral head. The threaded end 608 of the lag screw 602 engages the femoral head. As compression screw 604 is tightened, the threads 614 of the compression screw engage the threads of the cross hair screw 610 and lag screw 602, thereby moving the lag screw 602 in the general lateral direction toward the intramedullary nail providing compression to the femoral head. The cross hair screw 610 is then turned causing the compression screw 604 to move in the distal direction away from the lag screw 602. The fastener assembly 200 can alternatively be configured so that the compression screw 604 moves proximally relative to the lag screw 602. The compression screw 604 separate from the lag screw 602 helps to prevent rotation of the femoral head on the lag screw 602 by adding more area for resistance.

FIGS. 40-41 illustrate a fastener assembly 200 according to another embodiment of the invention having a lag screw 702 and a compression peg 704. The lag screw 702 includes an elongate body 706 and a threaded end 708. The elongate body 706 is semi-circular shaped in order to allow the compression peg 704 to be positioned partially inside the circumference of the lag screw 702 for insertion into the femur and has a key 712 positioned on the interior side of the elongate body 706. The elongate body 706 also has an aperture 710 through the body. The compression peg 704 is generally cylindrical and is sized to fit within the semi-circular body 706 of the lag screw. The key 712 of the lag screw is received by a slot 714 in the compression peg 704. The key 712 and slot 714 contain complimentary ratchet teeth.

In this embodiment, the lag screw 702 and the compression peg 704 are received simultaneously to slide in a proximal aperture of an intramedullary screw into a pre-drilled hole in the femur. The lag screw 702 extends across the break and into the femoral head. The threaded end of the lag screw 702 engages the femoral head. A compression tool similar to the tool describe in association with FIGS. 34-35 may be used to accomplish movement between the compression peg 704 and the lag screw 702, or between the entire assembly and the intramedullary nail 100. A set screw may used to fix the position of the fastener assembly. The set screw is configured such that when the set screw is tightened a protrusion on the set screw is received through the slot 710 of the lag screw 702 and moves the compression screw 704 away from the lag screw 702. The compression screw 704 separate from the lag screw 702 helps to prevent rotation of the femoral head on the lag screw by adding more area for resistance.

Figure 42:
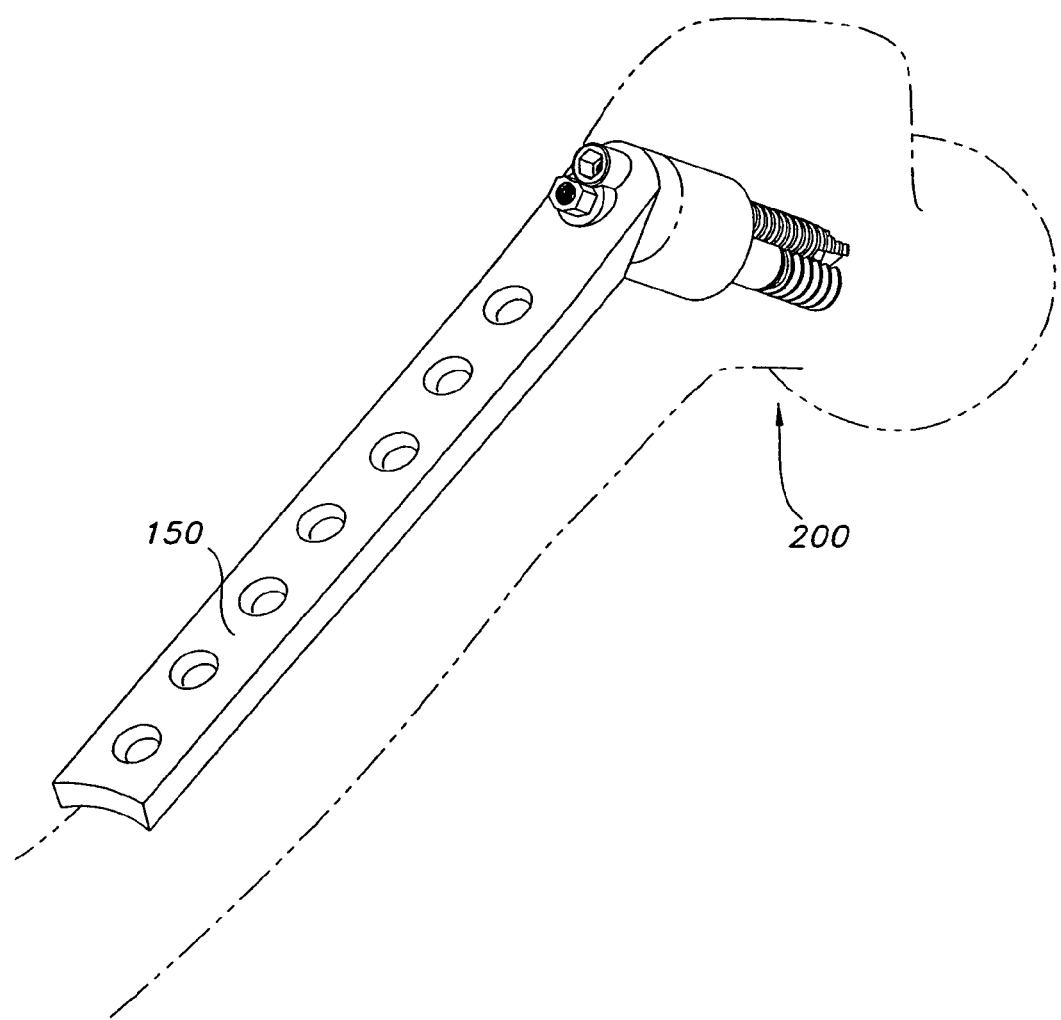
FIG. 42 is a perspective view of a compression plate according to an embodiment of the present invention which includes a fastener assembly according to an embodiment of the invention.

FIG. 42 illustrates another embodiment of the invention where a fastener assembly 200 is employed in cooperation with a compression plate 150. As illustrated, the devices are being applied to a femur. The various embodiments of the fastener assembly 200 disclosed above may be used with a similar compression plate, and various compression plates may be configured to be applicable to other parts of the anatomy.

Figure 43:
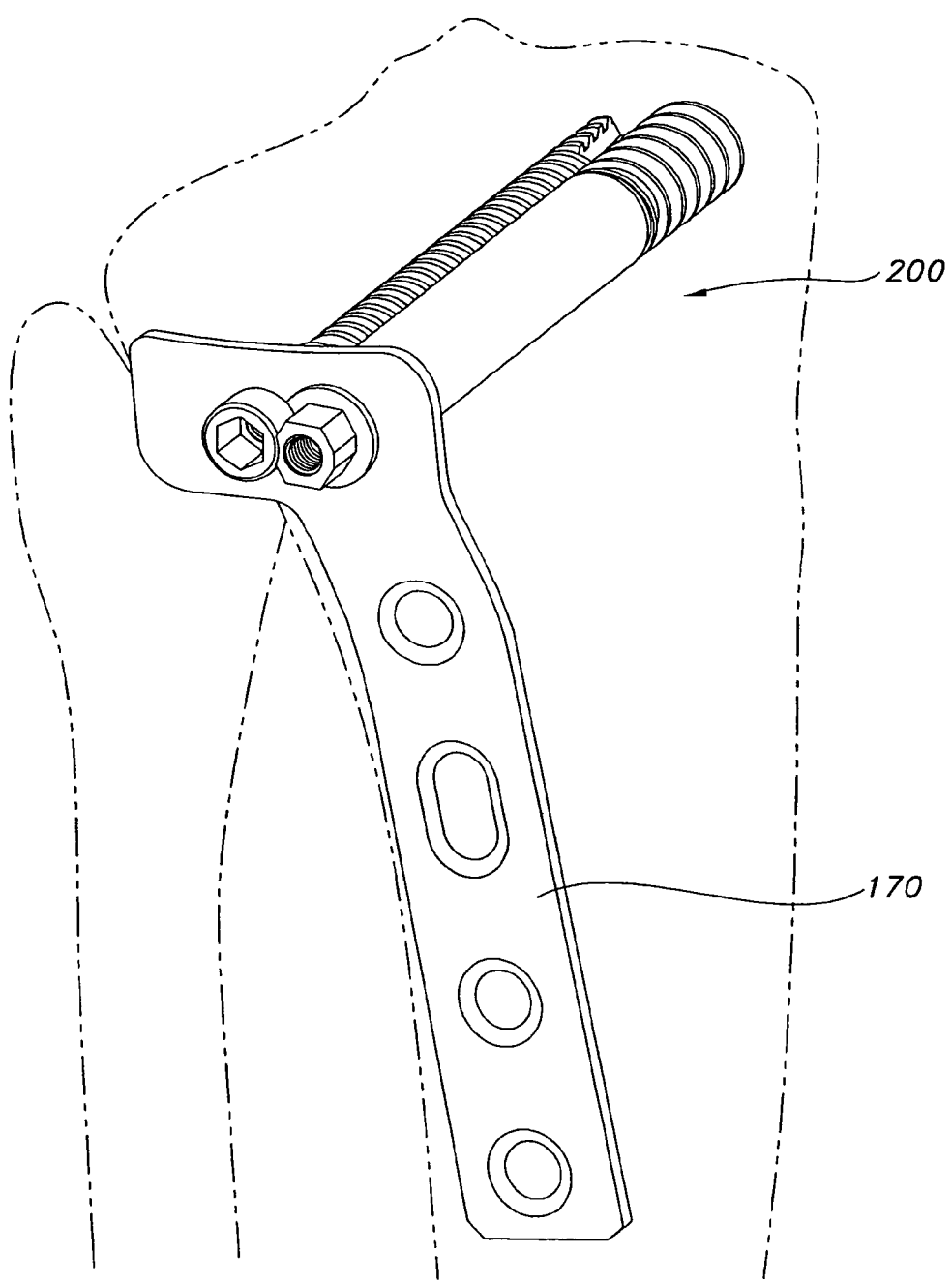
FIG. 43 is a perspective view of a periarticular plate according to an embodiment of the present invention which includes a fastener assembly according to an embodiment of the invention.

FIG. 43 illustrates another embodiment of the invention where a fastener assembly 200 is being used with a periarticular plate 170. The plate and fastener assembly shown are being applied to a proximal tibia. The various embodiments of the fastener assembly 200 disclosed above may be used with a similar periarticular plate and various periarticular plates may be configured to be applicable to other parts of the anatomy.

Figure 44:
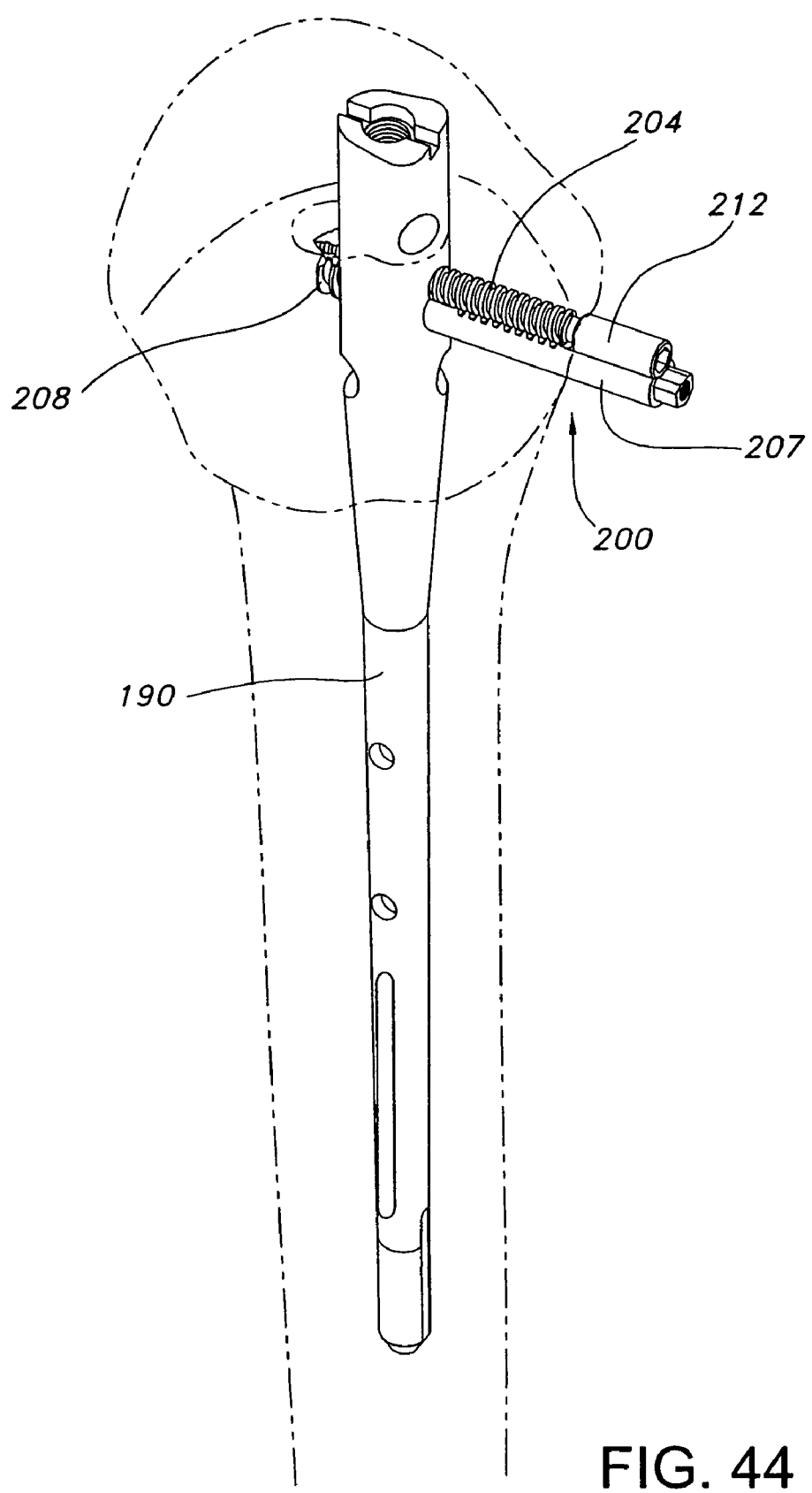
FIG. 44 is a perspective view of a device according to an embodiment of the present invention used in the context of humeral repair in a shoulder joint.

FIG. 44 illustrates another embodiment of the invention where a fastener assembly 200 is used in combination with a humeral nail 190. As illustrated, a head section 212 of compression screw 204 bears against the humerus to draw compression against the humerus. With the compression force applied to lag screw 202, and the lag screw 202 affixed to a bone fragment through its threaded end 208, the bone fragment may be drawn into position for proper healing. In some circumstances, it may be advantageous to place a washer or bearing surface (not shown) between the head section 212 and the humeral bone against which the head section 212 compresses. In yet another variant, the opening in the humerus may be enlarged such that head section 212 is permitted to penetrate the humerus and bear against a portion of the humeral nail 190. In such an embodiment, the fastener assembly 200 would be shorter than illustrated in FIG. 44 to obtain purchase in the same area of bone with the threaded end 208. The various embodiments of the fastener assembly 200 disclosed above may be used with a similar nail and various nails may be configured to be applicable to other parts of the anatomy.

As those skilled in the art will appreciate, the particular embodiments of this invention described above and illustrated in the figures are provided for explaining the invention and various alterations may be made in the structure and materials of the illustrated embodiments without departing from the spirit and scope of the invention as described above and in the following claims.

What is claimed is:

1. Apparatus for treating bone fractures, comprising:
  a. a bone implant adapted to be connected to a first bone portion and containing a transverse aperture;
  b. a fastening assembly having an engaging member and a compression member, the engaging member comprising an external channel on an elongate surface of the engaging member and a cooperation structure to cooperate with the compression member, wherein the compression member nests partially within the channel of the engaging member, the fastening assembly adapted to slide within the transverse aperture as a unit;
  c. wherein the engaging member engages a second bone portion and when installed the compression member contacts the second bone portion, and when the compression member is adjusted relative to the engaging member, the compression member contacts and interacts with a portion of the implant and the cooperation structure to thereby cause compression of the first and second bone portions relative to each other; and
  d. wherein the fastening assembly precludes rotation of the first and second bone portions relative to each other.

2. Apparatus according to claim 1 wherein when the compression member is adjusted relative to the engaging member, the compression member contacts and interacts with the cooperation structure, and a head of the compression member contacts and interacts with a shoulder within the transverse aperture to control sliding of the fastening assembly in the transverse aperture.

3. Apparatus according to claim 1 in which the compression member contacts and interacts with the engaging member to preclude the second bone portion from rotating relative to the engaging member.

4. Apparatus according to claim 1 in which the cooperation structure includes at least one of a key that cooperates with a slot on the compression member, a set of ratchet teeth that cooperates with a set of ratchet teeth on the compression member, a threaded portion that cooperates with a threaded portion on the compression member, or a cross hair screw that cooperates with a threaded portion on the compression member.

5. Apparatus according to claim 1 in which the compression member is adapted, when adjusted, to cooperate with the cooperation structure and thereby apply tension to the engaging member.

6. Apparatus according to claim 1 in which at least one of the compression member or the engaging member is a screw.

7. Apparatus according to claim 1 further comprising a set screw received in said implant, said set screw adapted to preclude sliding of the engaging member in the transverse aperture.

8. Apparatus according to claim 1 in which the transverse aperture is asymmetrical in cross section and includes a first portion adapted to receive at least part of the engaging member and a second portion adapted to receive at least part of the compression member.

9. Apparatus according to claim 1 in which the implant includes a proximal section that is asymmetrical in cross-section about at least one axis.

10. Apparatus according to claim 1, wherein the bone implant has a proximal end and a distal end and the compression member is positioned in the transverse aperture closer to the proximal end of the bone implant than the engaging member.

11. Apparatus according to claim 1, wherein the bone implant is an intramedullary nail.

12. Apparatus for treating a bone fracture, comprising:
 a. a bone implant adapted to be connected to a first bone portion and containing a transverse aperture;
 b. a fastening assembly adapted to be received in the transverse aperture, comprising:
  1. an engaging member adapted to slide in the implant transverse aperture and to engage a second bone portion; the engaging member including an external channel on an elongate surface of the engaging member and a cooperation structure to cooperate with a compression member;
  2. wherein the compression member nests partially within the channel of the engaging member,
 c. wherein the compression member
  1. contacts the second bone portion when installed in order, together with the engaging member, to preclude the second bone portion from rotating relative to the engaging member; and
  2. when the compression member is adjusted relative to the engaging member, the compression member contacts and interacts with a portion of the implant and the cooperation structure to control sliding of the fastening assembly in the transverse aperture.

13. Apparatus according to claim 12 wherein the cooperation structure contacts and cooperates with the engaging member to preclude the second bone portion from rotating relative to the first bone portion.

14. Apparatus according to claim 12 wherein when the compression member is adjusted relative to the engaging member, the compression member contacts and interacts with the cooperation structure, and a head of the compression member contacts and interacts with a shoulder within the transverse aperture to cause compression between the first bone portion and the second bone portion relative to each other.

15. Apparatus according to claim 12 in which the cooperation structure includes at least one of a key that cooperates with a slot on the compression member, a set of ratchet teeth that cooperates with a set of ratchet teeth on the compression member, a threaded portion that cooperates with a threaded portion on the compression member, or a cross hair screw that cooperates with a threaded portion on the compression member.

16. Apparatus according to claim 12 further comprising a set screw received in said implant, said set screw adapted to preclude sliding of the engaging member in the transverse aperture.

17. Apparatus according to claim 12 in which the transverse aperture is asymmetrical in cross section and contains a first portion adapted to receive at least part of the engaging member and a second portion adapted to receive at least part of the compression member.

18. Apparatus according to claim 12 in which the implant includes a proximal section which is asymmetrical in cross section about at least one axis.

19. Apparatus according to claim 12, wherein the bone implant has a proximal end and a distal end and the compression member is positioned in the transverse aperture closer to the proximal end of the bone implant than the engaging member.

20. Apparatus according to claim 12, wherein the bone implant is an intramedullary nail.

* * * * *

UNITED STATES PATENT AND TRADEMARK OFFICE
CERTIFICATE OF CORRECTION

PATENT NO.         : 7,527,627 B2                                        Page 1 of 1
APPLICATION NO.    : 10/936996
DATED              : May 5, 2009
INVENTOR(S)        : Joseph Ferrante It is certified that error appears in the above-identified patent and that said Letters Patent is hereby corrected as shown below:

Title Page, Column 2, under "Other Publications", delete "(tantum)))", and replace with -- (tantum) --; and Page 17, Column 10, Line 24, delete "215", and insert -- 215. --.

Signed and Sealed this

Twenty-first Day of July, 2009

JOHN DOLL
*Acting Director of the United States Patent and Trademark Office*